United States Patent
Matsuki et al.

(10) Patent No.: US 12,412,268 B2
(45) Date of Patent: Sep. 9, 2025

(54) TREATMENT SYSTEM, CONTROL DEVICE, AND CONTROL METHOD

(71) Applicant: OLYMPUS CORPORATION, Hachioji (JP)

(72) Inventors: Kenji Matsuki, Hachioji (JP); Yuto Hirabayashi, Suwa (JP); Shunsuke Matsui, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 417 days.

(21) Appl. No.: 17/859,824

(22) Filed: Jul. 7, 2022

(65) Prior Publication Data

US 2022/0343503 A1 Oct. 27, 2022

Related U.S. Application Data

(63) Continuation of application No. PCT/JP2020/000470, filed on Jan. 9, 2020.

(51) Int. Cl.
*G06T 7/00* (2017.01)
*A61B 1/00* (2006.01)
*G06T 7/90* (2017.01)
*A61B 18/00* (2006.01)

(52) U.S. Cl.
CPC ........ *G06T 7/0012* (2013.01); *A61B 1/00009* (2013.01); *G06T 7/90* (2017.01); *A61B 2018/00601* (2013.01); *A61B 2018/00708* (2013.01); *A61B 2018/00982* (2013.01); *G06T 2207/10068* (2013.01); *G06T 2207/20081* (2013.01); *G06T 2207/30004* (2013.01)

(58) Field of Classification Search
CPC ..................... G06T 7/0012; G06T 7/90; G06T 2207/10068; G06T 2207/20081;
(Continued)

(56) References Cited

U.S. PATENT DOCUMENTS

2012/0157890 A1 6/2012 Govari et al.
2014/0343416 A1 11/2014 Panescu et al.
(Continued)

FOREIGN PATENT DOCUMENTS

JP 4112762 * 7/2008
JP 4960112 B2 6/2012
(Continued)

OTHER PUBLICATIONS

Machine translation for JP JP 2015-000093 (Year: 2015).*
(Continued)

*Primary Examiner* — Qian Yang
(74) *Attorney, Agent, or Firm* — Oliff PLC

(57) ABSTRACT

A treatment system that includes a treatment instrument to apply a treatment energy to a living tissue from an end effector according to a supplied electric power to incise the living tissue, an imaging device to generate a captured image capturing a state in which the treatment energy is applied from the end effector to the living tissue, and a control device that includes a processor to control operation of the imaging device. The processor acquires the captured image, calculates a temporal change amount based on any one of a predetermined point and a predetermined area in the captured image as a determination value, determines whether incision of the living tissue has been completed based on the determination value, and in response to determining that incision of the living tissue has been completed, execute an instruction to stop supply of the electric power to the treatment instrument.

17 Claims, 16 Drawing Sheets

(58) Field of Classification Search
CPC ...... G06T 2207/30004; A61B 1/00009; A61B 2018/00601; A61B 2018/00708; A61B 2018/00982; A61B 2017/320093; A61B 17/320092; A61B 18/1445; A61B 2018/00678; A61B 2018/00988; A61B 2034/2065; A61B 2090/309; A61B 2090/3612

See application file for complete search history.

(56) References Cited

U.S. PATENT DOCUMENTS

2017/0280983 A1* 10/2017 Kawano ............. A61B 1/00158
2019/0046262 A1    2/2019 Hayashida et al.
2020/0275824 A1*  9/2020 Tata .................... A61B 1/0052

FOREIGN PATENT DOCUMENTS

| JP | 2012-125584 A |   | 7/2012  |
|----|---------------|---|---------|
| JP | 2015-000093   | * | 1/2015  |
| JP | 2016-523592 A |   | 8/2016  |
| WO | 2017/187523 A1|   | 11/2017 |
| WO | WO 2019/008629| * | 1/2019  |

OTHER PUBLICATIONS

Machine translation for JP 4112762 (Year: 2008).*
Machine translation for WO 2019/008629 (Year: 2019).*
Mar. 17, 2020 International Search Report issued in International Patent Application No. PCT/JP2020/000470.

\* cited by examiner

41(40)  Ar1  418  419  LT
              \____/
               415

41(40)

TREATMENT SYSTEM, CONTROL DEVICE, AND CONTROL METHOD

CROSS-REFERENCE TO RELATED APPLICATION

This application is a continuation of International Application No. PCT/JP2020/000470, filed on Jan. 9, 2020, the entire contents of which are incorporated herein by reference.

BACKGROUND

1. Technical Field

The present disclosure relates to a treatment system, a control device, and a control method.

2. Related Art

In the related art, a treatment instrument to incise a living tissue by applying a treatment energy to the living tissue from an end effector according to a supplied electric power has been known.

To treat a living tissue by using the treatment instrument, an operator causes a control device to supply an electric power to a treatment instrument by operating a foot switch or the like, to apply a treatment energy to a living tissue from an end effector. Moreover, the operator sees a captured image that is captured by an endoscope and displayed on a display device, and thereby recognizes whether incision of the living tissue has been completed. The operator then stops the supply of the electric power to the treatment instrument from the control device by operating the footswitch or the like.

SUMMARY

In some embodiments, a treatment system includes a treatment instrument configured to apply a treatment energy to a living tissue from an end effector according to a supplied electric power to incise the living tissue, an imaging device configured to generate a captured image capturing the living tissue during a state in which the treatment energy is applied from the end effector to the living tissue, and a control device including a processor configured to control operation of the imaging device, the processor being configured to: acquire the captured image from the imaging device, calculate a temporal change amount of the living tissue based on movement of the treatment instrument relative to any one of a predetermined point and a predetermined area in the captured image as a determination value, determine whether incision of the living tissue has been completed based on the determination value, and in response to determining that the incision of the living tissue has been completed, execute an instruction to stop supply of the electric power to the treatment instrument.

In some embodiments, a control device includes a processor configured to control operation of an imaging device when applying treatment energy by a treatment instrument to a living tissue from an end effector according to a supplied electric power to incise the living tissue. The processor is configured to acquire a captured image capturing the living tissue during a state in which the treatment energy is applied from the end effector to the living tissue, determine whether incision of the living tissue has been completed based on the captured image by calculating a temporal change amount of the living tissue based on movement of the treatment instrument relative to any one of a predetermined point and a predetermined area in the captured image, and execute an instruction to stop supply of the electric power to the treatment instrument in response to determining that the incision of the living tissue has been completed.

In some embodiments, provided is a control method that is performed by a processor of a control device. The method includes acquiring a captured image capturing a living tissue during a state in which a treatment energy is applied from an end effector to the living tissue, determining whether incision of the living tissue has been completed based on the captured image by calculating a temporal change amount of the living tissue based on movement of a treatment instrument relative to any one of a predetermined point and a predetermined area in the captured image, and executing an instruction to stop supply of an electric power to the treatment instrument in response to determining that the incision of the living tissue has been completed.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, modes to implement the disclosure (hereinafter, embodiments) will be explained with reference to the drawings. The embodiments explained below are not intended to limit the disclosure. Furthermore, like reference symbols are given to like parts throughout the description of the drawings.

First Embodiment

Schematic Configuration of Treatment System

Figure 1:
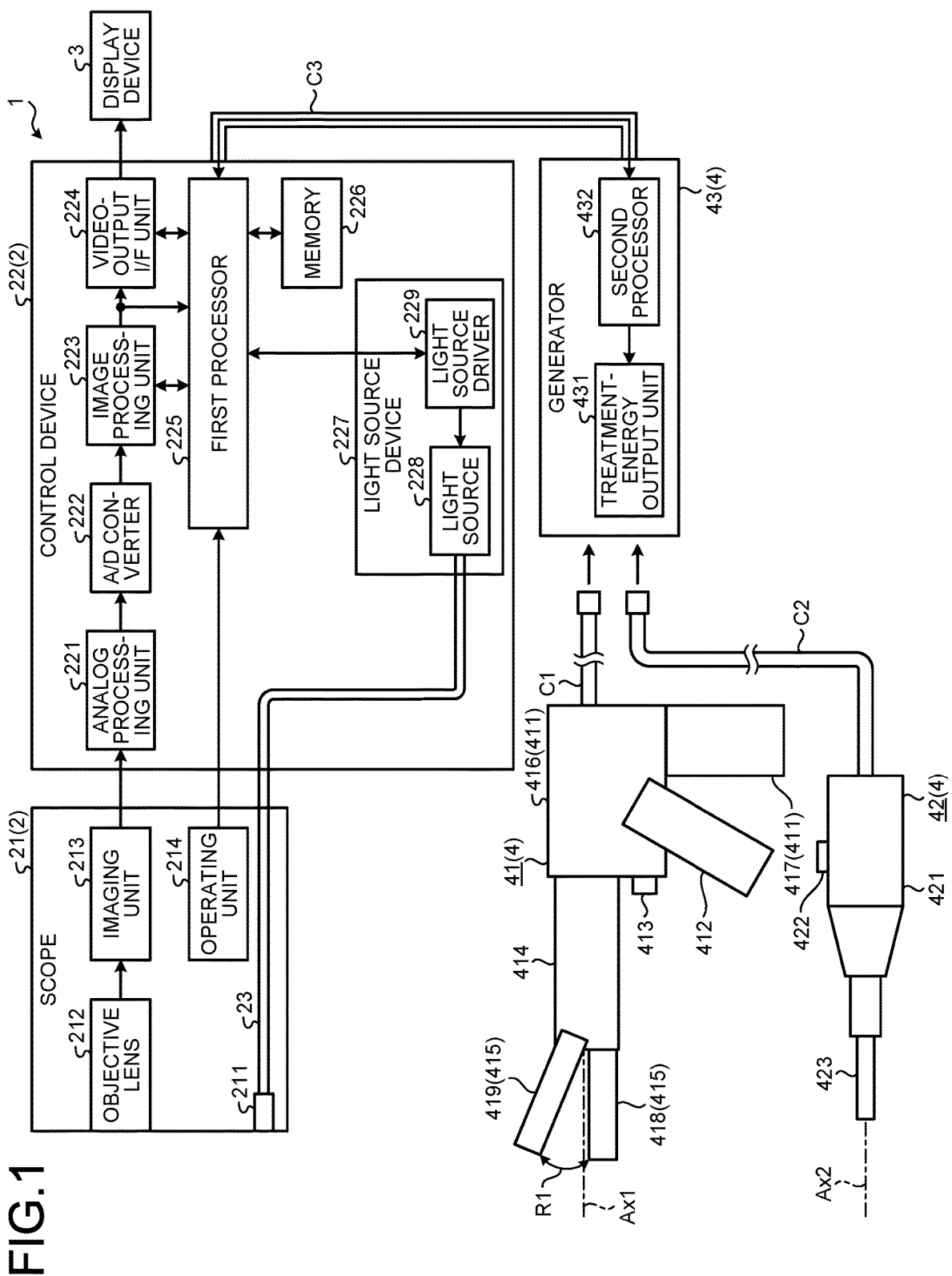
FIG. 1 is a diagram illustrating a treatment system according to a first embodiment.

FIG. 1 is a diagram illustrating a treatment system according to a first embodiment.

A treatment system 1 is a system that treats a living tissue to be treated (hereinafter, described as target site) in a living body while observing the inside of the living body. This treatment system includes an endoscope device 2, a display device 3, and a treatment device 4 as illustrated in FIG. 1.

Hereinafter, configurations of the endoscope device 2 and the treatment device 4 will be explained sequentially.

Configuration of Endoscope Device

The endoscope device 2 is a device to observe the inside of a living body. This endoscope device 2 includes a scope 21 and a control device 22 as illustrated in FIG. 1.

The scope 21 corresponds to an imaging device. This scope 21 is inserted into the living body, and captures an image of the inside of the living body. In the first embodiment, the scope 21 is flexible, and has a long thin shape, and is constituted of so-called flexible endoscope inserted into a living body. The scope 21 is detachably connected to the control device 22 by a connector (not illustrated). The scope 21 includes an illumination lens 211, an objective lens 212, an imaging unit 213, and an operating unit 214 as illustrated in FIG. 1.

The illumination lens 211 is arranged at a distal end of the scope 21, facing an emitting end of a light guide 23 (FIG. 1). Light emitted from the light guide 23 passes through the illumination lens 211, and then irradiated to the inside of a living body.

The objective lens 212 is arranged at a distal end of the scope 21. The objective lens 212 takes in light that has been irradiated to the inside of the living body from the illumination lens 211 and then reflected from the inside of the living body (subject image), to form an image on an acceptance surface of the imaging unit 213.

The imaging unit 213 generates a captured image by capturing the subject image formed by the objective lens 212 under control of the control device 22. The imaging unit 213 outputs the generated captured image to the control device 22.

The operating unit 214 has various kinds of switches (not illustrated) arrange therein to accept a user operation made by a user, such as a doctor. The operating unit 214 then outputs an operating signal according to the operation to the control device 22.

The control device 22 is constituted of a central processing unit (CPU), a field-programmable gate array (FPGA), and the like, and overall controls operation of the scope 21 and the display device 3. This control device 22 includes an analog processing unit 221, an A/D converter 222, an image processing unit 223, a video-output I/F unit 224, a first processor 225, a memory 226, and a light source device 227 as illustrated in FIG. 1.

The analog processing unit receives a captured image (analog signal) from the scope 21, and performs analog processing, such as clamp processing and noise removal processing (correlated double sampling (CDS)) with respect to the captured image.

The A/D converter 222 A/D converts the captured image (analog signal) subjected to the analog processing, and outputs the converted captured image (digital signal).

The image processing unit 223 performs various kinds of image processing with respect to a captured image input thereto, using various kinds of parameters for image processing that are stored in the memory 226, under control of the first processor 225. Examples of the various kinds of image processing include optical black subtraction processing, white balance (WB) adjustment processing, demosaicing processing, color matrix arithmetic processing, gamma correction processing, color reproduction processing, edge enhancement processing, and the like.

The video-output I/F unit 224 is constituted of a digital analog converter (DAC) encoder, or the like, and generates a video signal for display based on the captured image (digital signal) subjected to various kinds of image processing by the image processing unit 223. The video-output I/F unit 224 outputs the video signal for display to the display device 3.

The display device 3 is constituted of a display using liquid crystal, organic electroluminescence (EL), or the like. The display device 3 receives a video signal for display input therein from the video-output I/F unit 224, and displays a captured image based on the video signal for display.

The light source device 227 includes a light source 228 and a light source driver 229 as illustrated in FIG. 1. In the first embodiment, the light source device 227 is configured to be integrated in the control device 22, but not limited thereto, it may be configured to be independent from the control device 22.

The light source 228 is constituted of, for example, a white light emitting diode (LED) or the like, and emits light according to a supplied electric power. The light emitted from the light source 228 passes through the light guide 23 and the illumination lens 211, and then irradiated to the inside of a living body.

The light source driver 229 supplies an electric power to the light source 228 under control of the first processor 225.

The first processor 225 corresponds to a processor. The first processor 225 is constituted of, for example, a CPU, an FPGA, or the like and controls operation of the scope 21, operation of the display device 3, and overall operation of the control device 22. Moreover, the control device 22 and a generator 43 (FIG. 1) that constitutes the treatment device 4 are detachably connected to each other by a third electric cable C3 (FIG. 1). The first processor 225 controls operation of the generator 43 through the third electric cable C3. Detailed functions of the first processor 225 will be explained in "Control Method Performed by First Processor" described later.

The memory 226 stores a program executed by the first processor 225, information necessary for processing by the first processor 225, various kinds of parameters for the image processing described above, and the like.

[Configuration of Treatment Device]

The treatment device 4 treats a target site by applying a treatment energy to the target site. A treatment that can be performed by the treatment device 4 according to the first embodiment is a treatment for performing coagulation and incision of a target site, or a treatment for performing only incision of a target site. Hereinafter, for convenience of explanation, the treatment will be described as incision. Moreover, at least any one of an ultrasonic energy, a high frequency energy, and a thermal energy can be an example of the treatment energy. Applying an ultrasonic energy to a target site means applying an ultrasonic vibration to the target site. Moreover, applying a high frequency energy to a target site means applying a high frequency electric current to the target site. Furthermore, to apply a thermal energy to a target site means propagating heat generated by a heater or the like to the target site. This treatment device 4 includes a first treatment device 41 and a second treatment device 42, and the generator 43 as illustrated in FIG. 1.

The treatment device 4 is selectable to be used in a state in which the first treatment device 41 and the generator 43 are connected through the first electric cable C1 (FIG. 1) or a state in which the second treatment device 42 and the generator 43 are connected through the second electric cable C2 (FIG. 1) depending on a treatment method, a type of target site, and the like.

The first treatment device 41 corresponds to the treatment instrument, and is a clamp type treatment device that incises a target site while gripping the target site. The first treatment device 41 includes, as illustrated in FIG. 1, a first holding case 411, an operating knob 412, a first switch 413, a shaft 414, and a gripping portion 415.

The first holding case 411 supports the entire first treatment device 41. This first holding case 411 includes, as illustrated in FIG. 1, a holding-case main unit 416 that is positioned on a center axis Ax1 (FIG. 1) of the shaft 414, and a fixing handle 417 that extends downward from the holding-case main unit 416 in FIG. 1 and that is held by an operator.

The operating knob 412 is pivotably supported about the first holding case 411, and accepts an opening/closing operation by an operator.

The first switch 413 is arranged, being exposed to the outside from the first holding case 411, and accepts depression by the operator (hereinafter, described as first treatment-start operation). The first switch 413 outputs an operation signal according to the first treatment-start operation to the generator 43 through the first electric cable C1.

The shaft 414 has a cylindrical shape, and its end portion on a proximal end side (right side in FIG. 1) is connected to the holding case main unit 416. Moreover, to an end portion on a distal end side (left side in FIG. 1) of the shaft 414, the gripping portion 415 is attached. Inside the shaft 414, an opening closing mechanism (not illustrated) that causes a first and a second grippers 418, 419 constituting the gripping portion 415 to open and close according to an opening/closing operation made by an operator with respect to the operating knob 412 is arranged.

The gripping portion 415 corresponds to the end effector. This gripping portion 415 is a portion that incise a target site while gripping the target site. This gripping portion 415 includes the first and the second grippers 418, 419 as illustrated in FIG. 1.

The first and the second grippers 418, 419 correspond to a pair of grippers, and can grip a target site by opening and closing in a direction of an arrow R1 (FIG. 1) according to the opening closing operation by the operator made with respect to the operating knob 412. At least one of the first and the second grippers 418, 419 applies a treatment energy to a gripped target site under control of the generator 43. Thus, the target site is incised.

The second treatment device 42 corresponds to the treatment instrument, and is a non-clamp type device that incise a target site in a state in which it is in contact with the target site, being incapable of gripping a target site. This second treatment device 42 includes, as illustrated in FIG. 1, a second holding case 421, a second switch 422, and an end effector 423.

The second holding case 421 has a substantially cylindrical shape extending along a center axis Ax2, and supports the end effector 423.

The second switch 422 is arranged being exposed to the outside of the second holding case 421, and accepts depression by an operator (hereinafter, described as second treatment-start operation). The second switch 422 outputs an operation signal according to the second treatment-start operation to the generator 43 through the second electric cable C2.

The end effector 423 has a long shape extending along the center axis Ax2, and is attached inside the second holding case 421 in a state in which an end portion on a distal end side (left side in FIG. 1) is exposed to the outside. The end effector 423 applies a treatment energy to a target site from an end portion in a state in which the end portion on the distal end side is in contact with the target site under control of the generator 43. Thus, the target site is incised.

The generator 43 is constituted of a CPU, an FPGA, and the like, and overall controls operation of the first treatment device 41 connected through the first electric cable C1, or operation of the second treatment device 42 connected through the electric cable C2. This generator 43 includes a treatment-energy output unit 431 and a second processor 432 as illustrated in FIG. 1.

The treatment-energy output unit 431 supplies an electric power necessary for applying a treatment energy to a target site to the first treatment device 41 that is connected through the first electric cable C1, or to the second treatment device 42 that is connected through the second electric cable C2 under control of the second processor 432.

For example, when the first treatment device 41 is configured to apply an ultrasonic energy to a target site, the first treatment device 41 has an ultrasound transducer that generates an ultrasonic vibration according to an electric power supplied from the treatment-energy output unit 431. One of the first and the second grippers 418, 419 is constituted of a vibration transmission member that transmits the ultrasonic vibration, and applies the transmitted ultrasonic vibration to a target site gripped between the first and the second grippers 418, 419.

When the second treatment device 42 is configured to apply an ultrasonic energy to a target site, the second treatment device 42 has an ultrasound transducer that generates an ultrasonic vibration according to an electric power supplied from the treatment-energy output unit. The end effector 423 is constituted of a vibration transmission member that transmits the ultrasonic vibration, and applies the transmitted ultrasonic vibration to a target site.

Moreover, for example, when the first treatment device 41 is configured to apply a high frequency energy to a target site, the first and the second grippers 418, 419 respectively include an electrode to which an electric power is supplied from the treatment-energy output unit 431. As the electric power is supplied to the pair of electrodes, a high frequency current flows through a target site gripped between the pair of electrodes.

When the second treatment device 42 is configured to apply a high frequency energy to a target site, the end effector 423 includes an electrode that is supplied with an electric power from the treatment-energy output unit 431 to a portion between itself and a return electrode attached on a surface of a subject. As the electric power is supplied to the portion between the electrode and the return electrode, a high frequency current flows through a target site positioned between the end effector 423 and the return electrode.

Furthermore, for example, when the first treatment device 41 is configured to apply a thermal energy to a target site, at least one of the first and the second grippers 418, 419 has a heater that generates heat according to an electric power supplied from the treatment-energy output unit 431. At least one of the first and the second grippers 418, 419 transmits heat of the heater to a target site gripped between the first and the second grippers 418 and 419 according to the supply of the electric power.

When the second treatment device 42 is configured to apply a thermal energy to a target site, the end effector 423 has a heater that generates heat according to an electric power supplied from the treatment-energy output unit 431. The end effector 423 transmits heat of the heater to the target site according to the supply of the electric power.

The second processor 432 is constituted of, for example, a CPU, an FPGA, or the like. The second processor 432 performs incision control according to the first treatment-start operation by an operator with respect to the first switch 413, or the second treatment-start operation with respect to the second switch 422. The incision control is a control to incise a target site by causing the treatment-energy output unit 431 to supply an electric power to the first treatment device 41 or the second treatment device 42, and by applying a treatment energy to the target site.

[Control Method Performed by First Processor]

Next, a control method performed by the first processor 225 will be explained.

Figure 2:
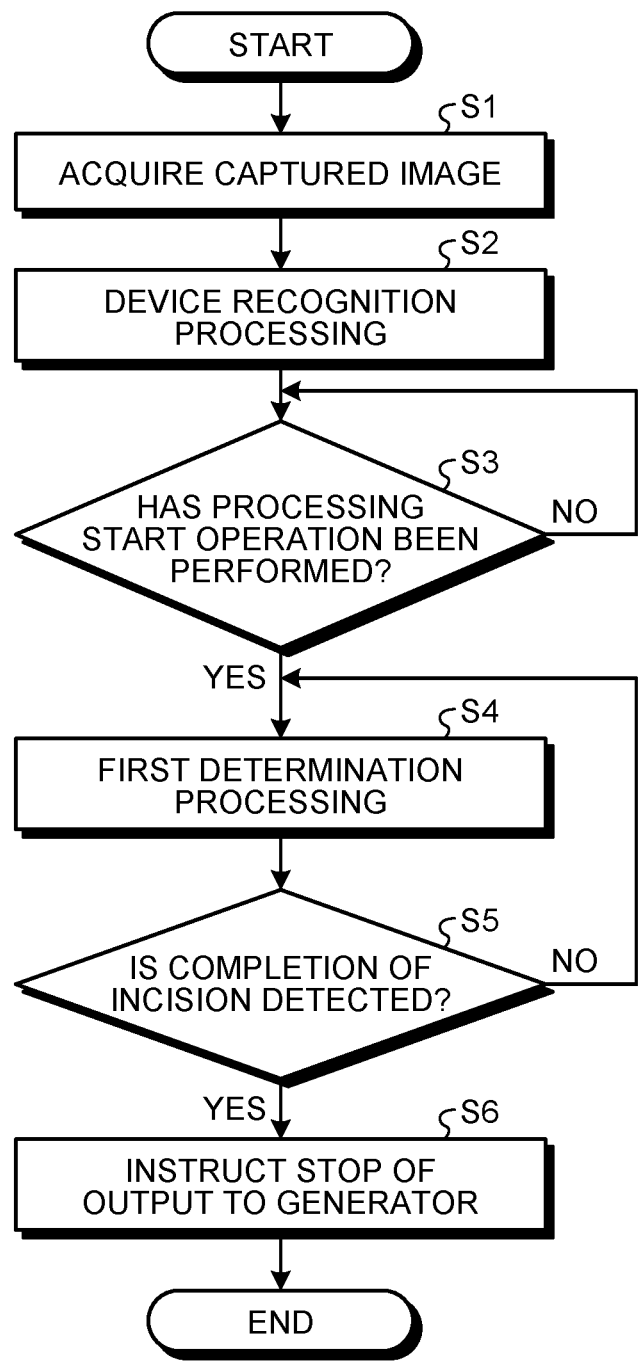
FIG. 2 is a flowchart illustrating a control method performed by a first processor.

FIG. 2 is a flowchart illustrating the control method performed by the first processor 225.

In the following, the first and the second treatment devices 41, 42 are collectively described as treatment device 40 for convenience of explanation.

First, the first processor 225 sequentially acquires captured images (digital signals) that capture the inside of a living body taken by the imaging unit 213, and that have passed through the analog processing unit 221, the A/D converter 222, and the image processing unit 223 in a frame unit (step S1).

In the first embodiment, at step S1, the first processor 225 acquires a captured image that captures the inside of a living body taken by the imaging unit 213, and that has passed through the analog processing unit 221, the A/D converter 222, and the image processing unit 223, but it is not limited thereto. For example, at step S1, the first processor 225 may acquire a captured image that captures the inside of a living body taken by the imaging unit 213, and that has passed through the analog processing unit 221 and the A/D converter 222 (captured image before subjected to various kinds of image processing by the image processing unit 223).

After step S1, the first processor 225 performs device recognition processing described below (step S2).

Figure 3:
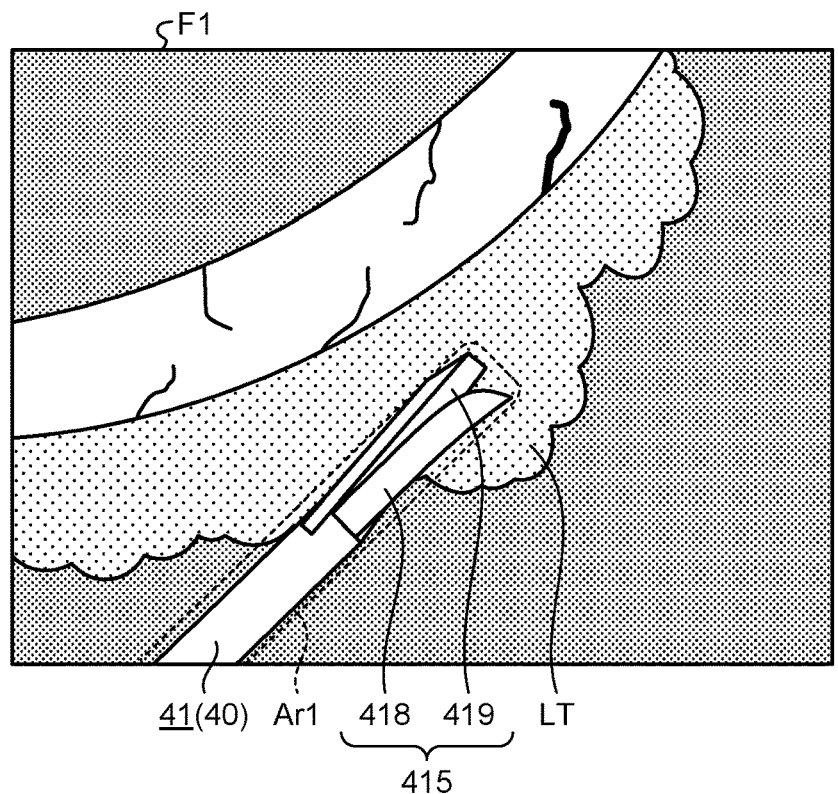
FIG. 3 is a diagram explaining device recognition processing (step S2)

FIG. 3 is a diagram explaining the device recognition processing (step S2). Specifically, FIG. 3 illustrates a captured image F1 acquired at step S1. In FIG. 3, a case in which the first treatment device 41 out of the first and the second treatment devices 41, 42 is used is illustrated.

First, the first processor 225 extracts, as illustrated in FIG. 3, an area Ar1 constituted of pixels having a pixel value of a specific color (for example, silver) unique to the treatment device 40 in the captured image F1.

Next, the first processor 225 determines whether the extracted area Ar1 extends linearly from an edge of the captured image F1.

When it is determined that it extends linearly from the edge of the captured image F1, the first processor 225 recognizes that the area Ar1 is the treatment device 40 (the first treatment device 41 in the case of FIG. 3) shown in the captured image F1.

The first processor 225 performs the device recognition processing (step S2) described above sequentially in a frame unit with respect to the captured image acquired sequentially at step S1.

After step S2, the first processor 225 monitors all the time whether the processing start operation (in the first embodiment, the first processing-start operation or the second processing-start operation) has been performed (step S3). When the first processing-start operation or the second processing-start operation has been performed, the second processor 432 starts incision control. That is, application of a treatment energy with respect to a target site LT (FIG. 3) from the gripping portion 415 or the end effector 423 is started. Moreover, the second processor 432 outputs a signal indicating that the treatment start operation has been performed to the first processor 225 through the third electric cable C3. The first processor 225 determines that the processing start operation has been performed based on the signal.

When it is determined that the treatment start operation has been performed (step S3: YES), the first processor 225 performs first determination processing described below (step S4).

Figure 4:
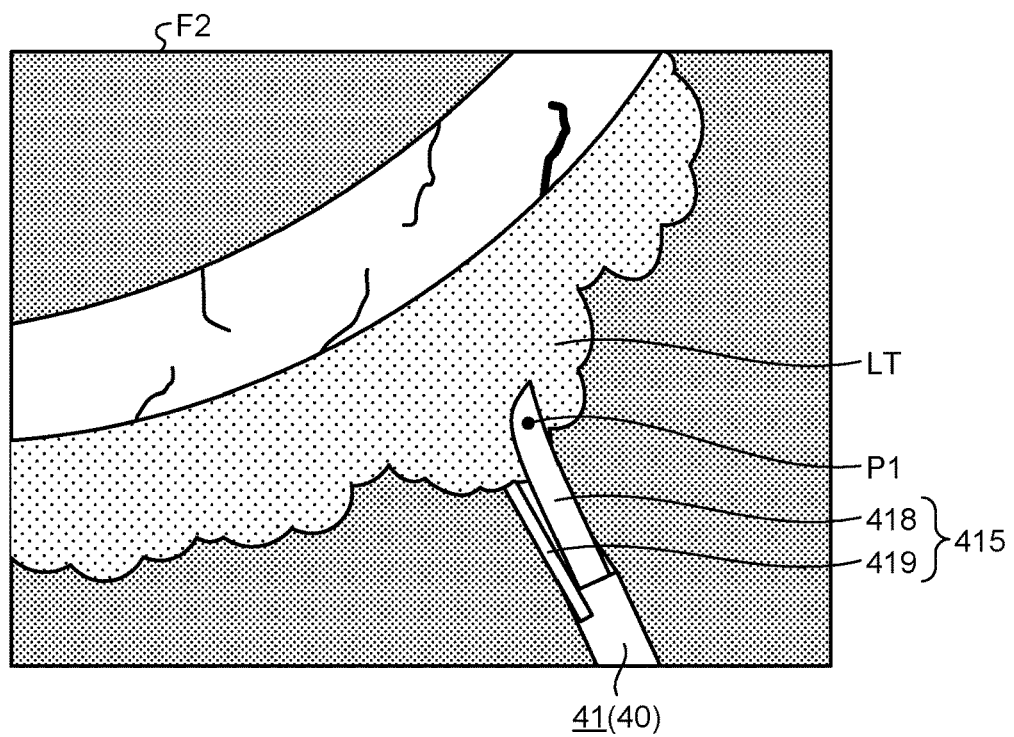
FIG. 4 is a diagram explaining first determination processing (step S4)
Figure 5:
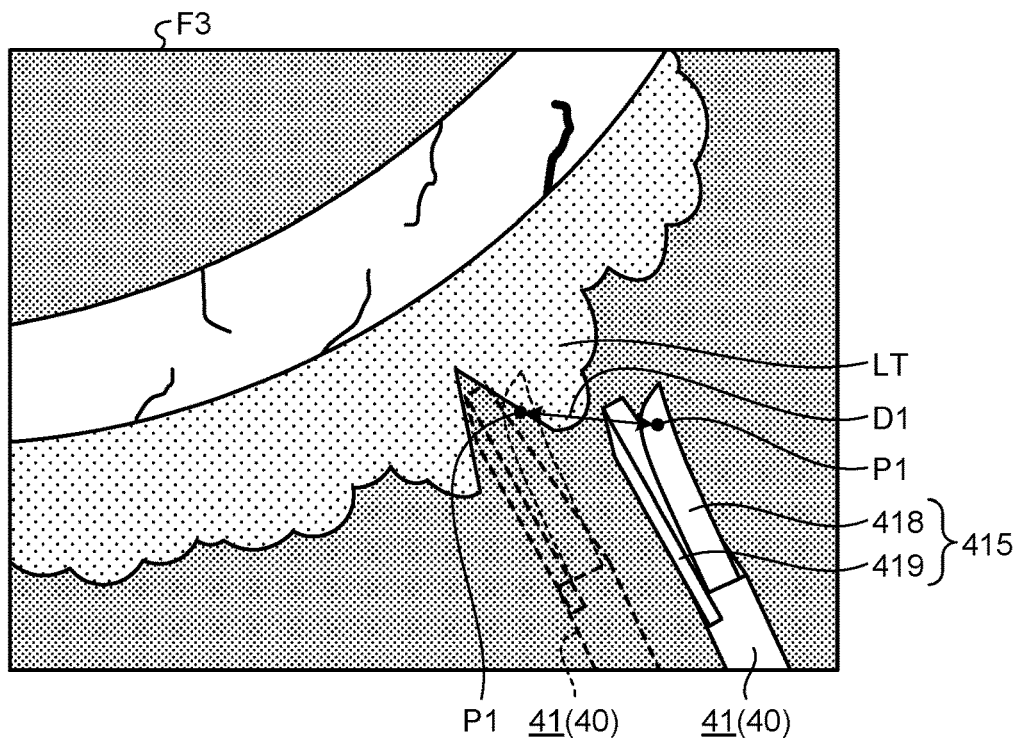
FIG. 5 is a diagram further explaining the first determination processing (step S4)
Figure 6:
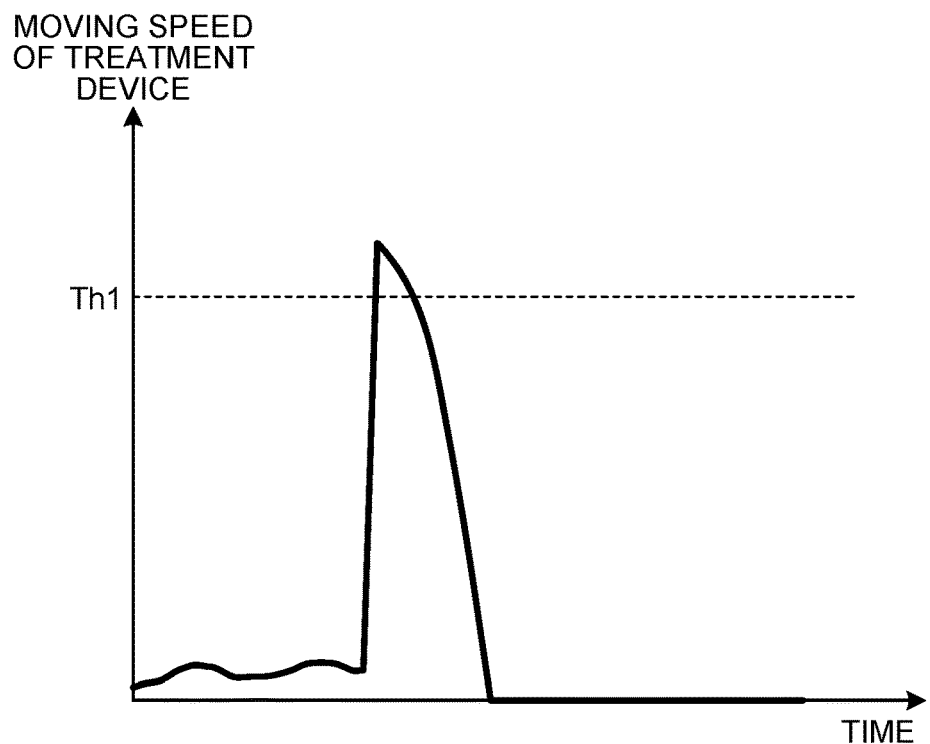
FIG. 6 is a diagram further explaining the first determination processing (step S4)

FIG. 4 to FIG. 6 are diagrams explaining the first determination processing (step S4). Specifically, FIG. 4 and FIG. 5 illustrate captured images F2, F3 that are acquired at step S1. Moreover, the captured image F2 illustrated in FIG. 4 is an image capturing a state before the target site LT is incised. The captured image F3 is an image capturing a state soon after the target site LT is incised. In FIG. 4 and FIG. 5, similarly to FIG. 3, a case in which the first treatment device 41 is used out of the first and the second treatment devices 41, 42 is illustrated. Furthermore, in FIG. 5, a position of the first treatment device 41 in the state illustrated in FIG. 4 is indicated by a broken line. FIG. 6 is a diagram illustrating a behavior of a moving speed of the treatment device 40 (the first treatment device 41 in the case of FIG. 4 and FIG. 5) after the treatment energy is started to be applied to the target site LT.

First, the first processor 225 identifies a feature point P1 (FIG. 4, FIG. 5) having a feature in pixel value or shape in the area Ar1 (the treatment device 40) extracted at step S2. The first processor 225 sequentially identifies the feature point P1 in a frame unit from the captured images acquired sequentially at step S1. The respective feature points P1 in the respective captured images (for example, the captured images F2, F3) are an identical portion on a subject (the treatment device 40).

Next, the first processor 225 calculates a moving speed of the treatment device 40 by dividing a difference (the number of pixels) D1 (FIG. 5) in coordinate value between the feature point P1 of a captured image (for example, the captured image F3) of the present frame (hereinafter, described as current frame) and the feature point P1 of a captured image next previous to the current frame (for example, the captured image F2) by time between the frames. The first processor 225 sequentially calculates the moving speed of the treatment device 40 for the captured images acquired sequentially at step S1 in a frame unit. The moving speed of the treatment device 40 corresponds to a determination value.

The moving speed of the treatment device described above is calculated based on the captured image of the current frame and the captured image of the next previous frame, but it is not limited thereto, and it may be calculated based on a captured image of the current frame and a captured image several frames before the current frame.

Next, the first processor 225 compares the calculated moving speed of the treatment device 40 with a first threshold Th (FIG. 6) sequentially. When the moving speed of the treatment device 40 becomes equal to or higher than the threshold Th1, the first processor 225 determines that incision of the target site LT has been completed (detects completion of incision of the target site LT). The first threshold Th1 is stored in the memory 226 as information necessary for processing of the first processor 225.

When the target site LT is to be incised by using the clamp type first treatment device 41, an operator first makes the target site LT be under tension, while gripping the target site LT with the first and the second grippers 418, 419 (state illustrated in FIG. 4). After setting this condition, the operator performs the first processing-start operation with respect to the first switch 413. Therefore, as it is found when FIG. 4 and FIG. 5 are compared, the first and the second grippers 418, 419 move at a high speed by reaction when the target site LT is incised as they have been pulling the target site LT. In other words, when the target site LT is incised, the moving speed of the treatment device 40 described above momentary becomes equal to or higher than the first threshold Th1 as illustrated in FIG. 6.

When completion of incision of the target site LT is detected (step S5: YES), the first processor 225 instructs the generator 43 (the second processer 432) to stop the output to through the third electric cable C3 (step S6). Thus, the second processor 432 stops supply of an electric power to the treatment device 40 (stops the operation of the treatment-energy output unit 431).

According to the first embodiment explained above, following effects are obtained.

The control device 22 according to the first embodiment determines whether incision of the target site LT has been completed based on a captured image (for example, the captured images F1 to F3) capturing a state in which the treatment energy is applied to the target site LT by the gripping portion 415 or the end effector 423, and stops the supply of the electric power to the treatment device 40 when it is determined that incision of the target site LT has been completed. That is, determination whether incision of the target site LT has been completed is not performed by visual confirmation by an operator, but is performed by the control device 22 and, furthermore, stop of supply of an electric power to the treatment device 40 is not performed by an operation by the operator, but is performed by the control device 22.

Therefore, a time lag from completion of incision of the target site LT to stop of supply of an electric power to the treatment device 40 can be resolved. Accordingly, it is possible to avoid supply of unnecessary power to the treatment device 40, and to reduce a load on the treatment device 40.

Moreover, in the control device 22 according to the first embodiment, the moving speed of the treatment device 40 described above is adopted as a determination value.

Therefore, by using a typical phenomenon that occurs at the time of incision of the target site LT in the treatment device 40, completion of incision of the target site LT can be favorably determined. The typical phenomenon is, as described above, a phenomenon that "the first and the second grippers 418, 419 move at a high speed by reaction when the target site LT is incised as they have been pulling the target site LT".

Moreover, in the control device 22 according to the first embodiment, out of subjects taken in the captured images (for example, the captured images F1 to F3), an object extending linearly from an edge of the captured image is detected as the first and the second grippers 418, 419 (the device recognition processing (step S2)).

Therefore, by using a typical way of appearance of the treatment device 40 shown in the captured image, the treatment device 40 can be favorably recognized.

Second Embodiment

Next, a second embodiment will be explained.

In the following explanation, identical reference symbols are given to components similar to those of the first embodiment described above, and their detailed explanation will be omitted or simplified.

Figure 7:
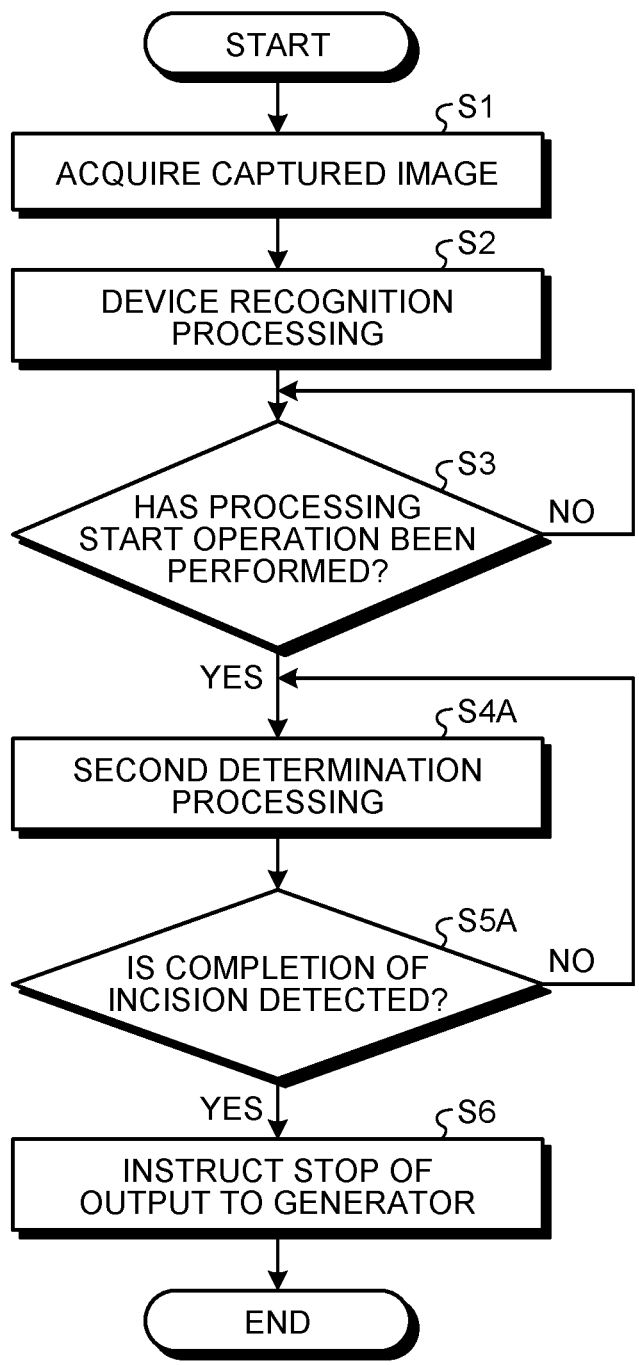
FIG. 7 is a flowchart illustrating a control method according to a second embodiment.

FIG. 7 is a flowchart illustrating a control method according to the second embodiment.

In the second embodiment, as illustrated in FIG. 7, a control method performed by the first processor 225 is different from the first embodiment described above.

In the control method according to the second embodiment, as illustrated in FIG. 7, steps S4A, S5A are adopted instead of steps S4, S5 in the control method (FIG. 2) explained in the first embodiment described above. In the following, steps S4A, S5A will be explained mainly.

Step S4A is performed when it is determined that the processing start operation has been performed (step S3: YES).

Specifically, the first processor 225 performs second determination processing described below at step S4A.

Figure 8:
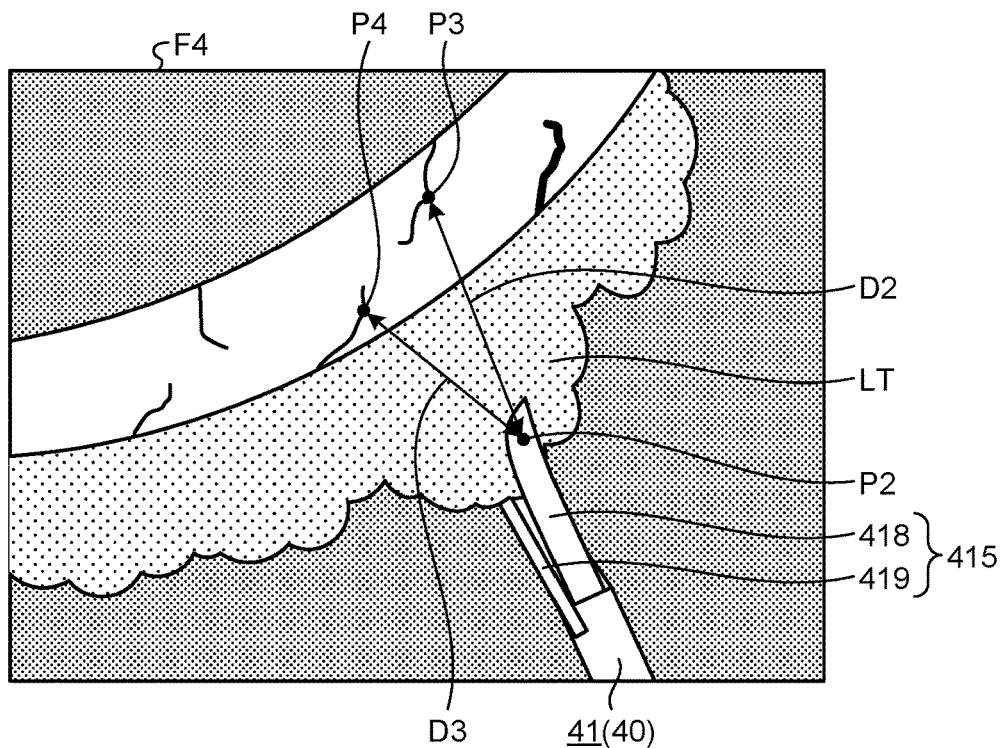
FIG. 8 is a diagram explaining second determination processing (step S4A)
Figure 9:
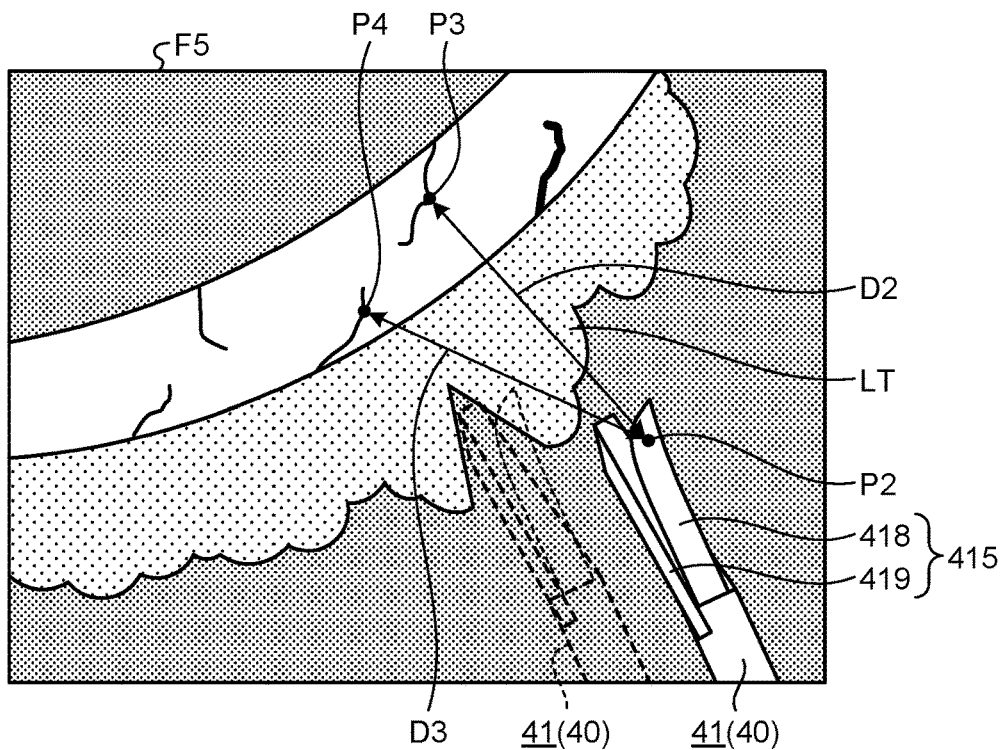
FIG. 9 is a diagram further explaining the second determination processing (step S4A)

FIG. 8 and FIG. 9 are diagrams explaining the second determination processing (step S4A). Specifically, FIG. 8 an FIG. 9 illustrate captured images F4, F5 acquired at step S1. Moreover, the captured image F4 illustrated in FIG. 8 is an image capturing a state similar to that of the captured image F2 illustrated in FIG. 4. The captured image F5 illustrated in FIG. 9 is an image capturing a state similar to that of the captured image F3 illustrated in FIG. 5.

First, the first processor 225 identifies a feature point P2 (FIG. 8, FIG. 9) having a feature in pixel value and shape in the area Ar1 (the treatment device 40) extracted at step S2. The first processor 225 sequentially identifies the feature point P2 in a frame unit from the captured images sequentially acquired at step S1. The respective feature points P2 in the respective captured images (for example, the captured images F4, F5) are an identical portion on a subject (the treatment device 40).

Next, the first processor 225 identifies feature points P3, P4 (FIG. 8, FIG. 9) having a feature in pixel value and shape in the target site LT adjacent to the area Ar1 (the treatment device 40) extracted at step S2. The first processor 225 sequentially identifies the feature points P3, P4 (FIG. 8, FIG. 9) in a frame unit from the captured images sequentially acquired at step S2. The first processor 225 sequentially identifies the feature points P3, P4 in a frame unit from the captured images sequentially acquired at step S1. The respective feature points P3 identified in the respective captured images (for example, the captured images F4, F5) are an identical portion on a subject (the target site LT). Similarly, the respective feature points P4 identified in the respective captured images (for example, the captured images F4, F5) are an identical portion on the subject (the target site LT).

Next, the first processor 225 calculates a distance (the number of pixels) D2 between the feature points P2 and P3, and a distance (the number of pixels) D3 between the feature points P2 and P4, respectively in the captured images of the same frame (for example, the captured image F4 or the captured image F5). The first processor 225 sequentially performs calculation of the distances D2, D3 in a frame unit in the captured images sequentially acquired at step S1.

Next, the first processor 225 calculates a first moving speed of the treatment device 40 by dividing a difference (the number of pixels) between the difference D2 in the captured image of the current frame (for example, the captured image F5) and the distance D2 in the captured image of the next previous frame (for example, the captured image F4) by time between the frames. The first moving speed of the treatment device 40 means a moving speed of the treatment device 40 (the feature point P2) relative to the feature point P3 as a reference point. The first processor 225 sequentially performs calculation of the first moving speed of the treatment device 40 in a frame unit for the captured images sequentially acquired at step S1.

The treatment device 40 explained above corresponds to a determination value.

The first and the second moving speeds of the treatment device 40 described above are respectively calculated based on the captured image of the current frame and the captured image of the next previous frame, but not limited thereto, they may respectively be calculated based on the captured image of the current frame and a captured image several frames before the current frame.

Next, the first processor 225 sequentially compares the calculated first and second moving speeds of the treatment device 40 with the first threshold Th1. The first processor 225 detects completion of incision of the target site LT when both the first and the second moving speeds of the treatment device 40 become equal to or higher than the first threshold Th1.

When completion of incision of the target site LT is detected (step S5A: YES), the first processor 225 shifts to step S6.

According to the second embodiment explained above, besides effects similar to those of the first embodiment described above, following effects are obtained.

In the control device 22 according to the second embodiment, the first and the second moving speeds of the treatment device 40 relative to the feature points P3, P4 in the target site LT are adopted as the determination value.

Therefore, an influence of hand shake of a scopist holding the scope 21 with hands can be cancelled, and completion of incision of the target site LT can be accurately determined.

Particularly, the first and the second moving speeds of the treatment device 40 are adopted as the determination value. Therefore, for example, compared to when only one of the first and the second moving speeds is adopted as the determination value, as more than one value is used as the determination value, erroneous determination is suppressed, and completion of incision of the target site LT can be more accurately determined.

Third Embodiment

Next, a third embodiment will be explained.

In the following explanation, identical reference symbols are given to components similar to those of the first embodiment described above, and their detailed explanation will be omitted or simplified.

Figure 10:
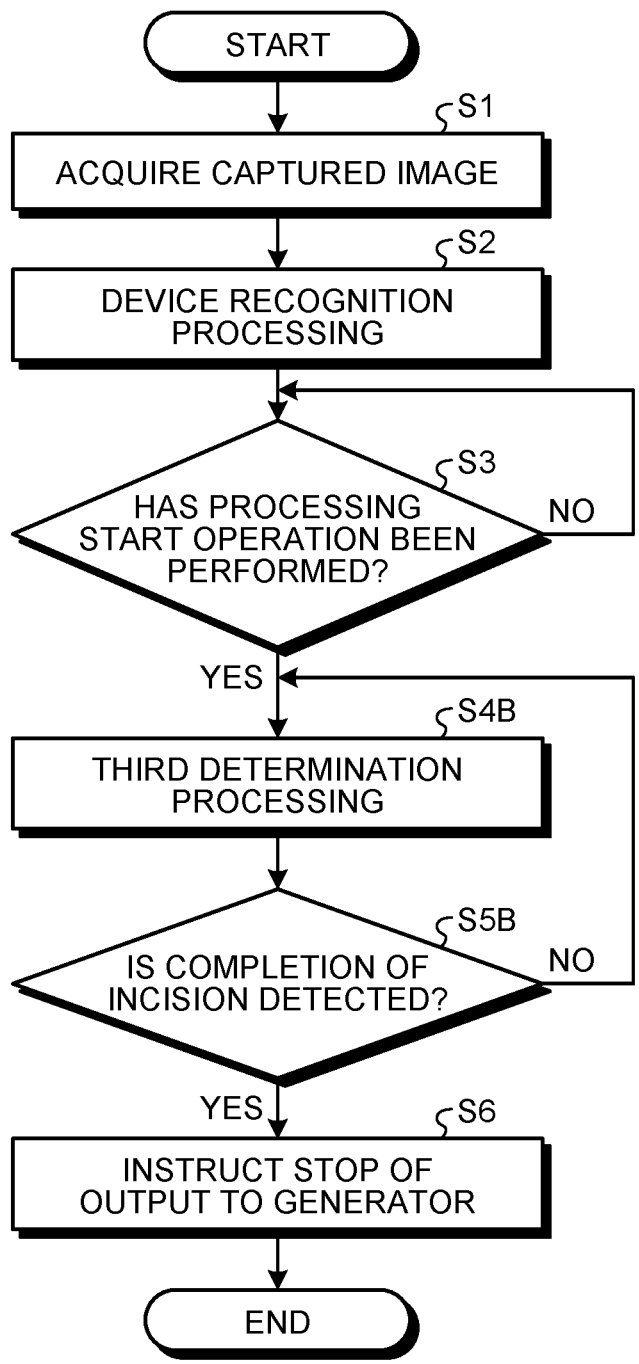
FIG. 10 is a flowchart illustrating a control method according to a third embodiment.

FIG. 10 is a flowchart illustrating a control method according to a third embodiment.

In the third embodiment, as illustrated in FIG. 10, the control method performed by the first processor 225 is different from that of the first embodiment described above.

In the control method according to the third embodiment, as illustrated in FIG. 10, steps S4B, S5B are adopted instead of steps S4, S5 in the control method (FIG. 2) explained in the first embodiment described above. In the following, steps S4B, S5B will be explained mainly.

Step S4B is performed when it is determined that the processing start operation has been performed (step S3: YES).

Specifically, the first processor 225 performs third determination processing described below at step S4B.

Figure 11:
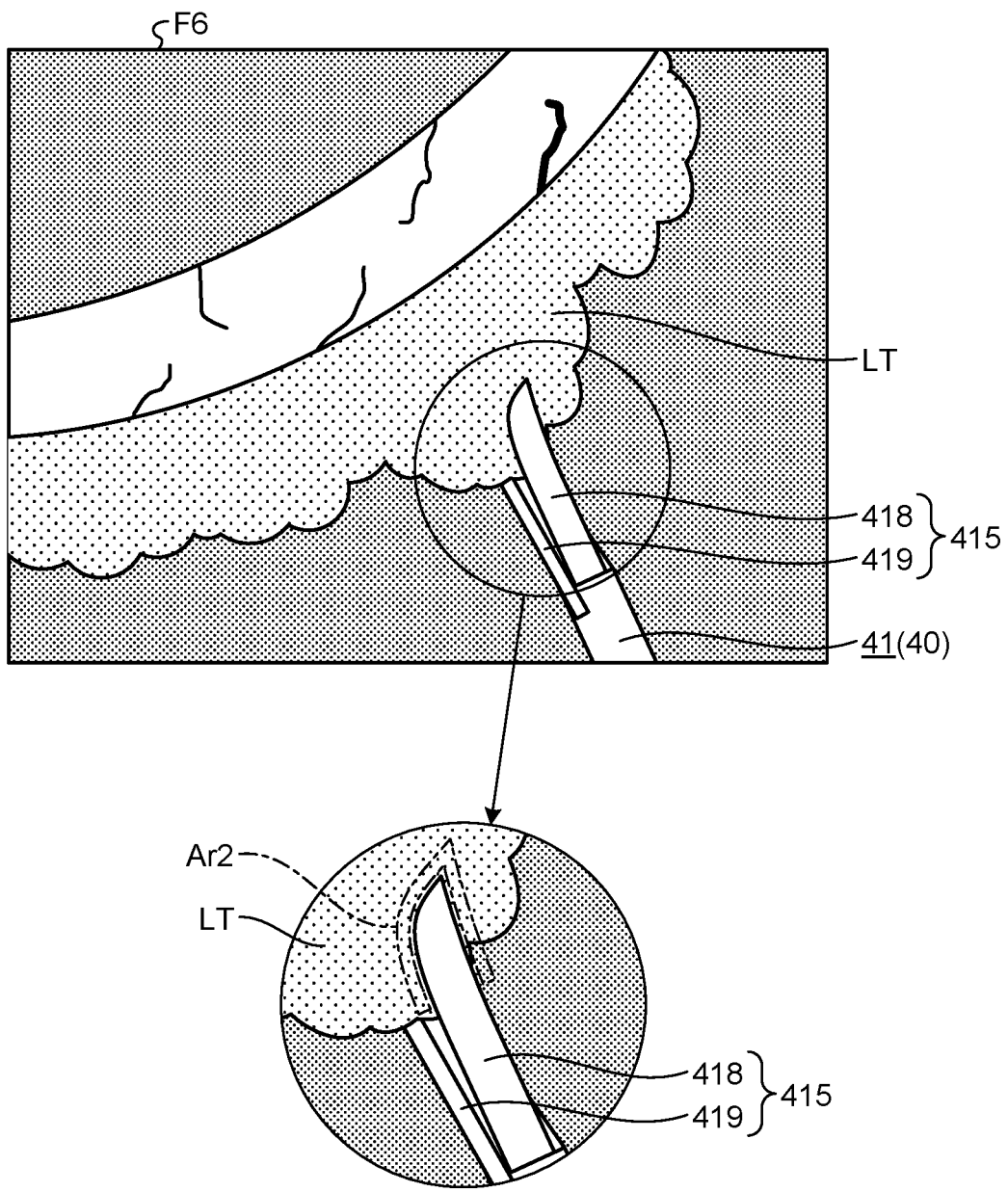
FIG. 11 is a diagram explaining third determination processing (step S4B)
Figure 12:
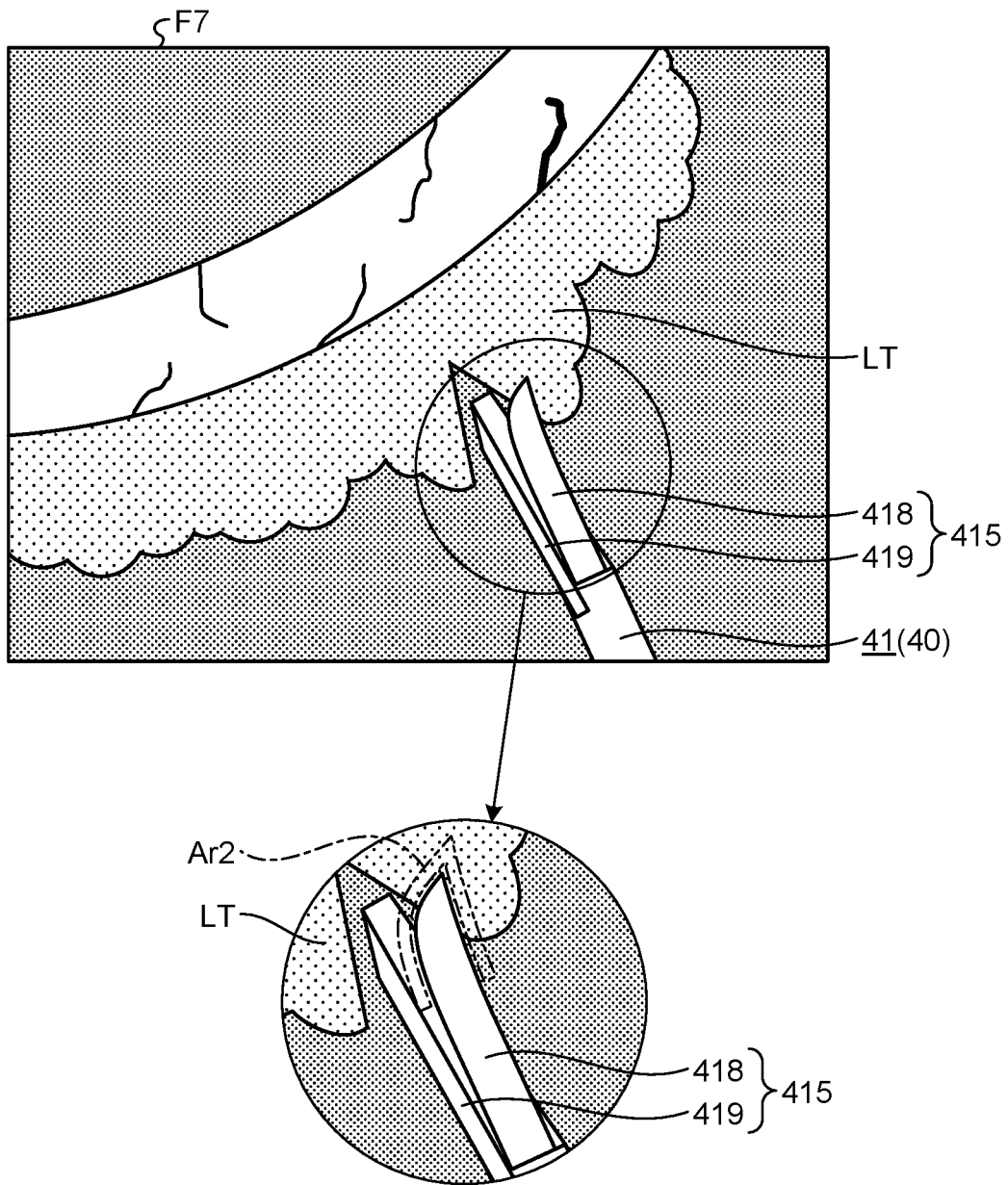
FIG. 12 is a diagram further explaining the third determination processing (step S4B)
Figure 13:
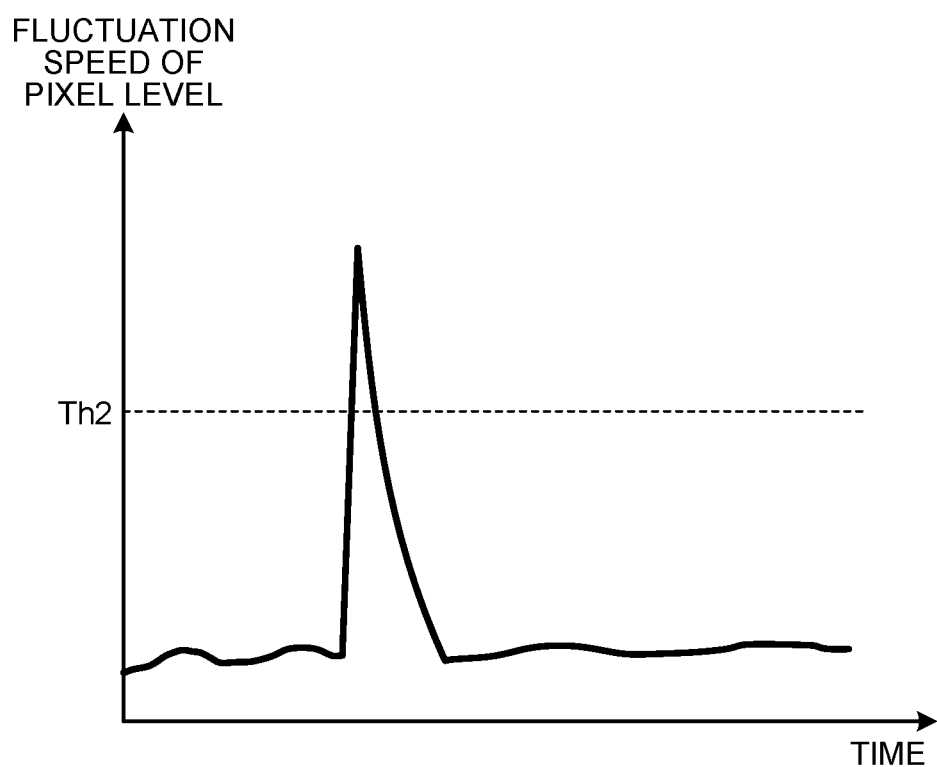
FIG. 13 is a diagram further explaining third determination processing (step S4B)

FIG. 11 to FIG. 13 are diagrams explaining the third determination processing (step S4B). Specifically, FIG. 11 an FIG. 12 illustrate captured images F6, F7 acquired at step S1. Moreover, the captured image F6 illustrated in FIG. 11 is an image capturing a state similar to that of the captured image F2 illustrated in FIG. 4. The captured image F7 illustrated in FIG. 12 is an image capturing a state similar to that of the captured image F3 illustrated in FIG. 5. FIG. 13 is a diagram illustrating a behavior of fluctuation speed of pixel level in an area Ar2 (FIG. 11, FIG. 12) after application of a treatment energy to the target site LT.

First, the first processor 225 identifies the area Ar2 (FIG. 11, FIG. 12) adjacent to the area Ar1 (the treatment device 40) extracted at step S2. The first processor 225 sequentially identifies the area Ar2 in a frame unit from the captured images sequentially acquired at step S1. The respective areas Ar2 identified in the respective captured images (for example, the captured images F6, F7) are areas having an identical positional relationship with respect to the respective areas Ar1 (the treatment device 40) extracted in the respective captured images.

Next, the first processor 225 calculates a mean value of pixel level of respective pixels in the area Ar2 in the captured image (for example, the captured image F6 or the captured image F7) of the same frame. Examples of the pixel level include a pixel value (RGB value) of a pixel, a brightness value according to a Y signal (brightness signal). The first processor 225 sequentially performs calculation of a mean value of the pixel level of the respective pixels in the area Ar2 in a frame unit for the captured images sequentially acquired at step S1.

Next, the first processor 225 calculates a fluctuation speed of pixel level by dividing a difference between the mean value of pixel level of the respective pixels in the area Ar2 in the captured image of the current frame (for example, the captured image F7) and the mean value of pixel level of the respective pixels in the area Ar2 in the captured image of the next previous frame (for example, the captured image F6) by time between the frames. The fluctuation speed of pixel value corresponds to the determination value.

The fluctuation speeds of pixel level described above is calculated based on a captured image of the current frame and a captured image of the next previous frame, but not limited thereto, they may respectively be calculated based on a captured image of the current frame and a captured image several frames before the current frame.

Next, the first processor 225 sequentially compares the calculated fluctuation speeds of pixel level with a second threshold Th2 (FIG. 13). The first processor 225 detects completion of incision of the target site LT when the fluctuation speed of pixel level becomes equal to or higher than the second threshold Th2. The second threshold Th2 is stored in the memory 226 as information necessary for the processing of the first processor 225.

When the target site LT is incised, as it is found when FIG. 11 and FIG. 12 are compared, the target site LT adjacent to the gripping portion 415 is incised to be separated, and respectively moves apart from the gripping portion 415 quickly. In other words, because the target site LT that has been present in the area Ar2 rapidly moves away and disappears therefrom when the target site LT is incised, the fluctuation speed of pixel level described above momentary becomes equal to or higher than the second threshold Th2 as illustrated in FIG. 13.

When completion of incision of the target site LT is detected (step S5B: YES), the first processor 225 shifts to step S6.

According to the third embodiment explained above, besides effects similar to those of the first embodiment described above, following effects are obtained.

In the control device 22 according to the third embodiment, the fluctuation speed of pixel level is adopted as the determination value.

Therefore, also when the non-clamp type second treatment device 42 other than the clamp type first treatment device 41 that incise the target site LT in a state in which the target site LT is pulled while gripping the target site LT is used, completion of incision of the target site LT can be favorably detected.

Fourth Embodiment

Next, a fourth embodiment will be explained.

In the following explanation, identical reference symbols are given to components similar to those of the first embodiment described above, and their detailed explanation will be omitted or simplified.

Figure 14:
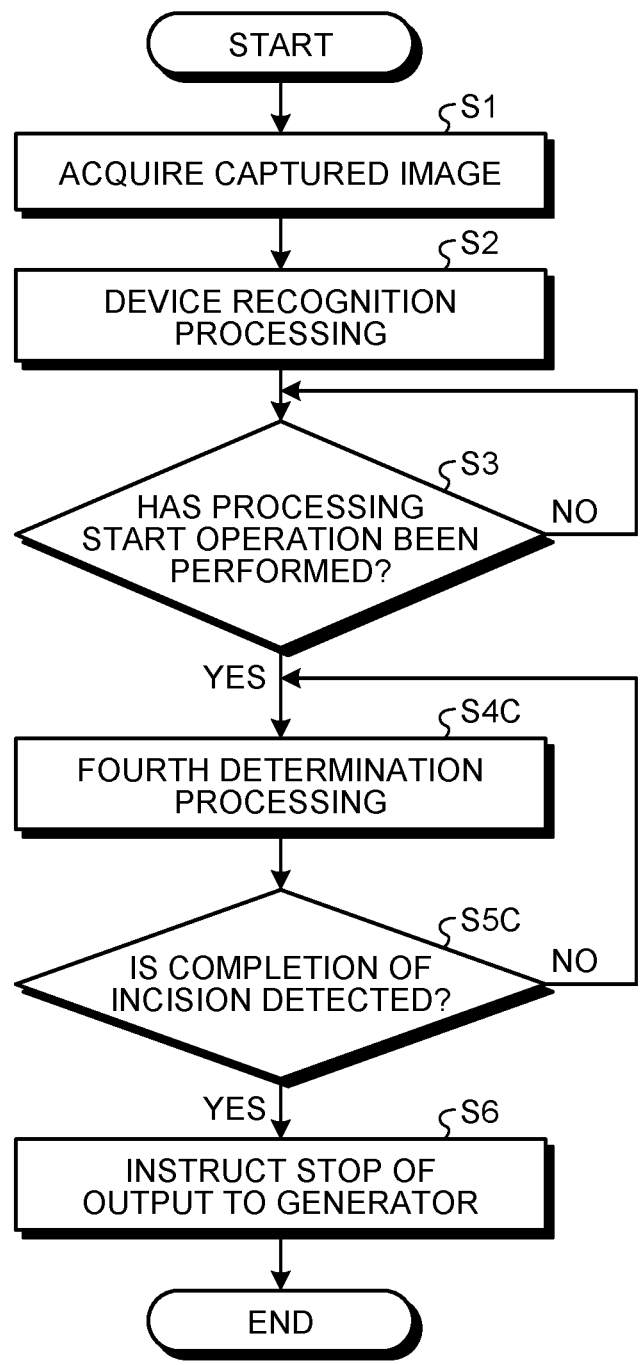
FIG. 14 is a flowchart illustrating a control method according to a fourth embodiment.

FIG. 14 is a flowchart illustrating a control method according to the fourth embodiment.

In the fourth embodiment, as illustrated in FIG. 14, the control method performed by the first processor 225 is different from the first embodiment described above.

In the control method according to the fourth embodiment, as illustrated in FIG. 14, steps S4C, S5C are adopted instead of steps S4, S5 in the control method (FIG. 2) explained in the first embodiment described above. In the following, steps S4C, S5C will be explained mainly.

Step S4C is performed when it is determined that the processing start operation has been performed (step S3: YES).

Specifically, the first processor 225 performs fourth determination processing described below at step S4C.

Figure 15:
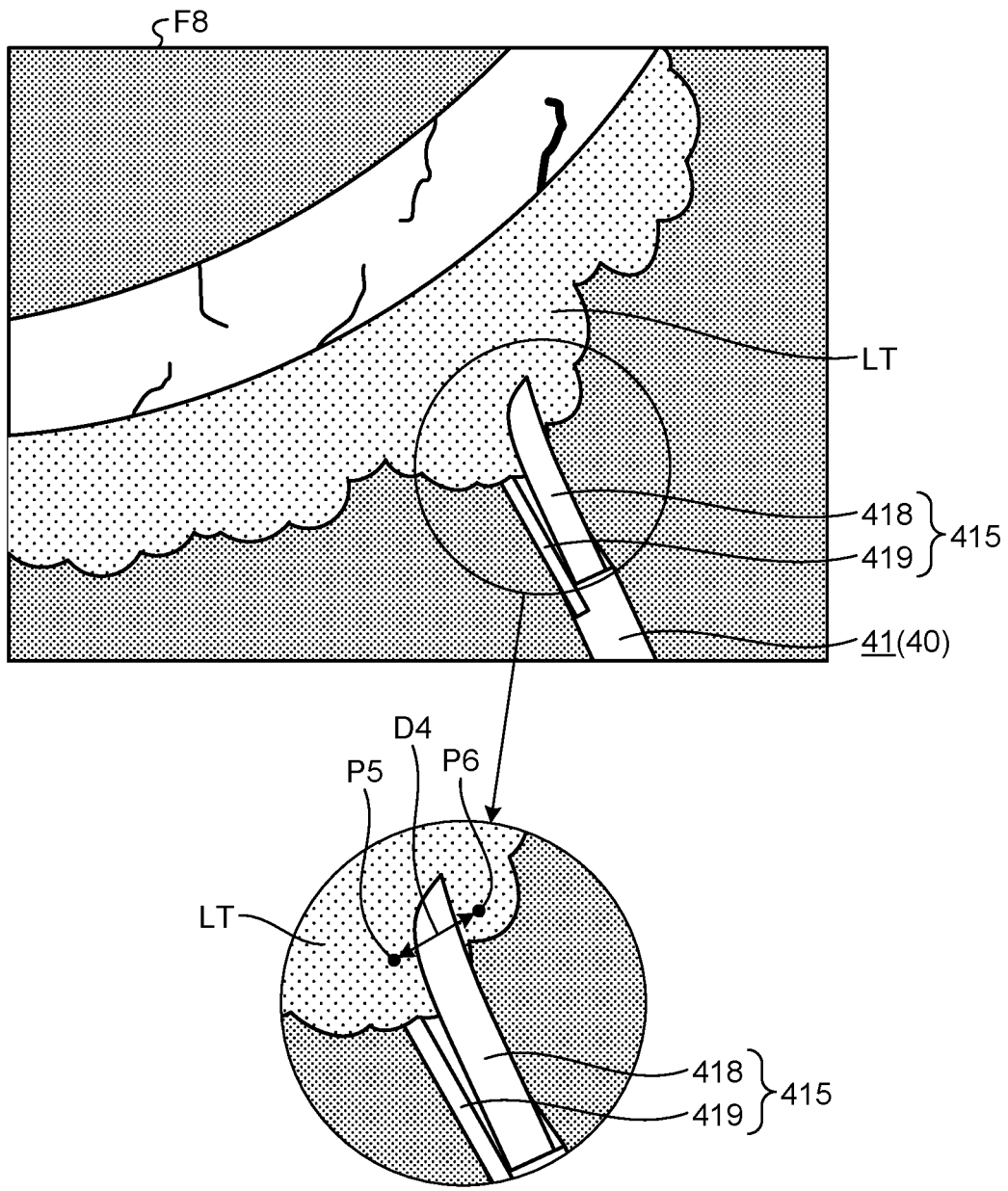
FIG. 15 is a diagram explaining fourth determination processing (step S4C)
Figure 16:
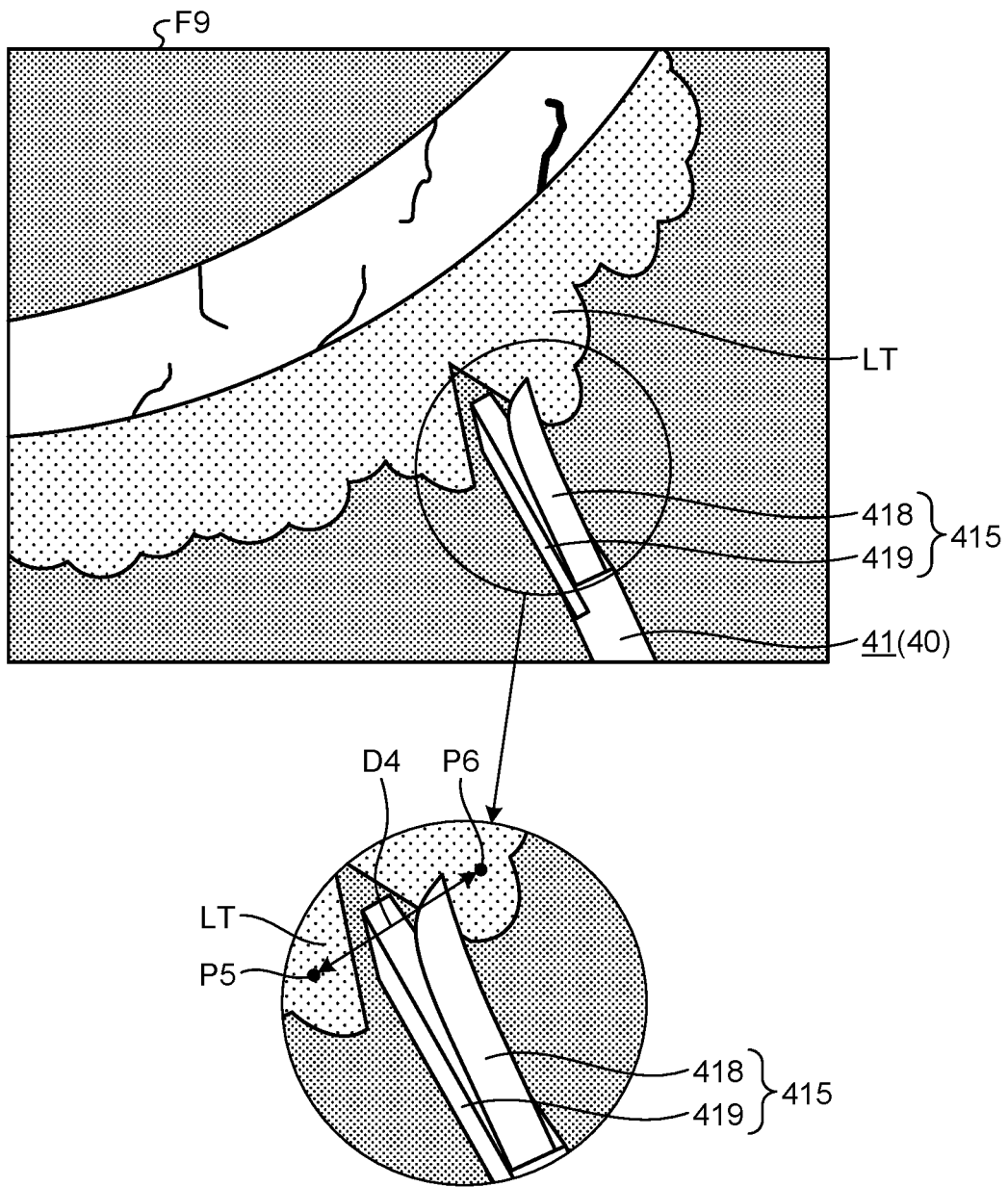
FIG. 16 is a diagram further explaining the fourth determination processing (step S4C)

FIG. 15 and FIG. 16 are diagrams explaining the fourth determination processing (step S4C). Specifically, FIG. 15 an FIG. 16 illustrate captured images F8, F9 acquired at step S1. Moreover, the captured image F8 illustrated in FIG. 15 is an image capturing a state similar to that of the captured image F2 illustrated in FIG. 4. The captured image F9 illustrated in FIG. 16 is an image capturing a state similar to that of the captured image F3 illustrated in FIG. 5.

First, the first processor 225 identifies a feature points P5, P6 (FIG. 15, FIG. 16) having a feature in pixel value and shape in the target site LT adjacent to the area Ar1 (the treatment device 40) extracted at step S2. The first processor 225 sequentially identifies the feature points P5, P6 in a frame unit from the captured images sequentially acquired at step S1. The respective feature points P5 identified in the respective captured images (for example, the captured images F8, F9) are an identical portion on a subject (the target site LT). Similarly, the respective feature points P6 identified in the respective captured images (for example, the captured images F8, F9) are an identical portion on a subject (the target site LT).

Next, the first processor 225 calculates a distance (the number of pixels) D4 between the feature points P5 and P6 in the captured image of the same frame (for example, the captured image F8 or the captured image F9). The first processor 225 sequentially performs calculation of the distance D4 in a frame unit in the captured images sequentially acquired at step S1.

Next, the first processor 225 calculates a moving speed of the target site LT by dividing a difference (the number of pixels) between the distance D4 in the captured image of the current frame (for example, the captured image F9) and the distance D4 in the captured image of the next previous frame (for example, the captured image F8) by time between the frames. The first processor 225 sequentially calculates the moving speed of the target site LT for the captured images acquired sequentially at step S1 in a frame unit. The moving speed of the target site LT corresponds to the determination value.

The moving speed of the target site LT described above is calculated based on the captured image of the current frame and the captured image of the next previous frame, but not limited thereto, it may be calculated based on the captured image of the current frame and a captured image several frames before the current frame.

Next, the first processor 225 sequentially compares the calculated moving speed of the target site LT with a third threshold Th3. The first processor 225 detects completion of incision of the target site LT when the moving speed of the target site LT becomes equal to or higher than the third threshold Th3. The third threshold is stored in the memory 226 as information necessary for the processing of the first processor 225.

When the target site LT is incised, as it is found when FIG. 15 and FIG. 16 are compared, the target site LT adjacent to the gripping portion 415 is incised to be separated, and respectively moves apart from the gripping portion 415 at a high speed. In other words, when the target site LT is incised, the moving speed of the target site LT described above momentary becomes equal to or higher than the third threshold Th3.

When completion of incision of the target site LT is detected (step S5C: YES), the first processor 225 shifts to step S6.

Also when the moving speed of the target site LT described above is adopted as the determination value as in the fourth embodiment explained above, effects similar to those of the first and the third embodiments can be obtained.

Fifth Embodiment

Next, a fifth embodiment will be explained.

In the following explanation, identical reference symbols are given to components similar to those of the first embodiment described above, and their detailed explanation will be omitted or simplified.

Figure 17:
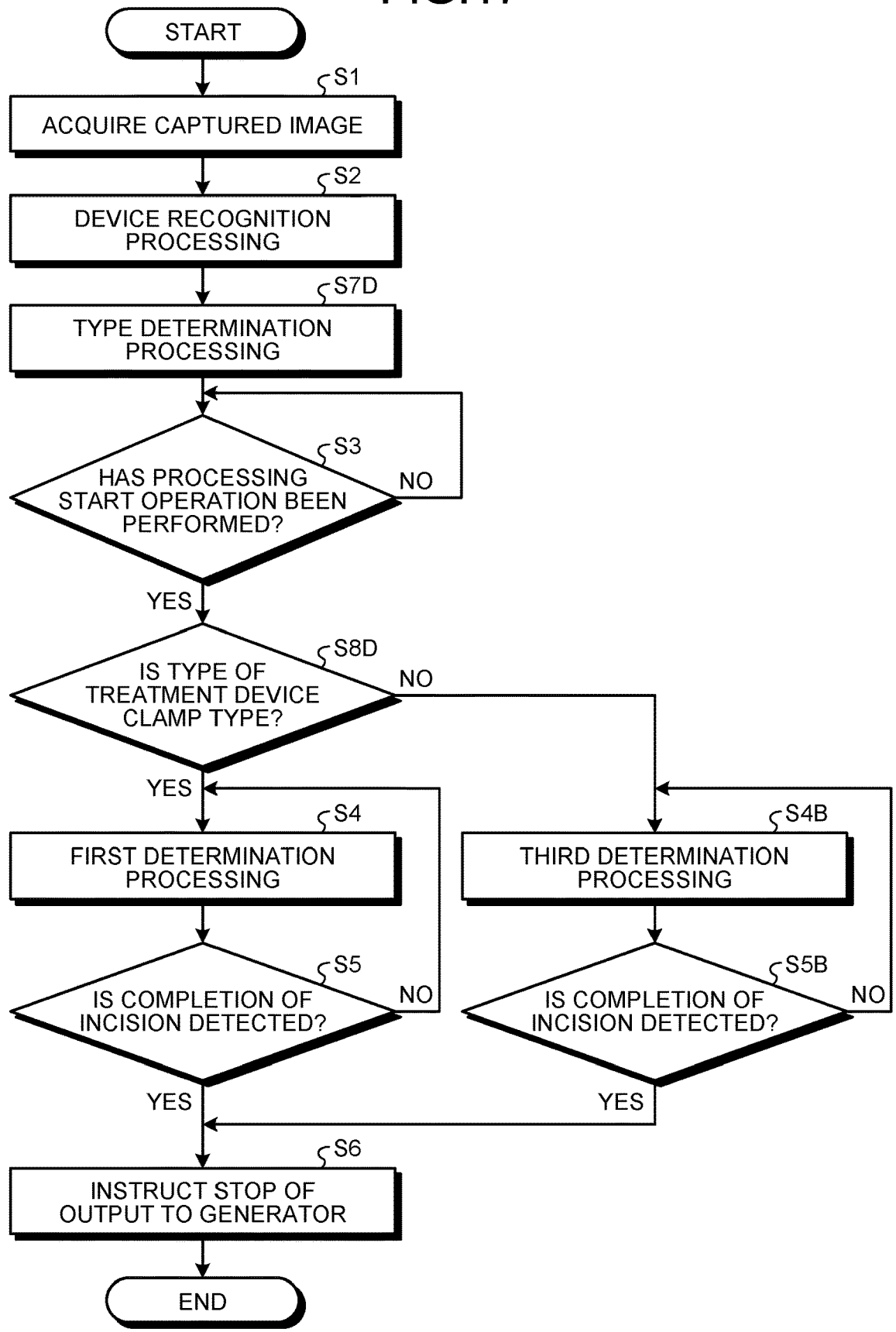
FIG. 17 is a flowchart illustrating a control method according to a fifth embodiment.

FIG. 17 is a flowchart illustrating a control method according to the fifth embodiment.

In the fifth embodiment, as illustrated in FIG. 17, the control method performed by the first processor 225 is different from the first embodiment described above.

In the control method according to the fifth embodiment, as illustrated in FIG. 17, steps S7D, S8D and steps S4B, S5B explained in the third embodiment described above are added to the control method (FIG. 2) explained in the first embodiment described above. In the following, steps S7D, S8D will be explained mainly.

In the fifth embodiment, a training model described below is stored in the memory 226 as information necessary for processing of the first processor 225.

The training model is provided for each type of the treatment device 40 (type of the first treatment device 41; clamp type, type of the second treatment device 42: non-clamp type), and is a model that is trained by machine learning (for example, deep learning, or the like) to learn a feature of the treatment device 40 based on captured image (training image) capturing the treatment device 40. The first processor 225 is enabled to determine the type of the treatment device 40 (type of the first treatment device 41: clamp type, type of the second treatment device 42: non-clamp type) shown in a captured image by image recognition n (artificial intelligence (AI)) using the training model.

Step S7D is performed after the device recognition processing (step S2).

Specifically, the first processor 225 performs type determination processing to determine the type of the treatment device 40 (type of the first treatment device 41: clamp type, type of the second treatment device 42: non-clamp type) shown in a captured image acquired at step S1, by the image recognition using the training model stored in the memory 226 (step S7D).

Thereafter, the first processor 225 shifts to step S3.

Step S8D is performed when the processing start operation has been performed (step S3: YES).

Specifically, the first processor 225 determines whether the type of the treatment device 40 shown in the captured image is determined by the type determination processing (step S7D) as the clamp type (step S8D).

When the type of the treatment device 40 is determined as the clamp type (step S8D: YES), the first processor 225 shifts to step S4.

On the other hand, when the treatment device 40 is determined as the non-clamp type (step S8D: NO), the first processor 225 shifts to step S4B. When completion of incision of the target site LT is detected at step S4B (step S5B: YES), the first processor 225 shifts to step S6.

According to the fifth embodiment explained above, besides effects similar to those of the first embodiment described above, following effects are obtained.

According to the control device 22 according to the fifth embodiment, because the type determination processing (step S7D) described above is performed, appropriate determination processing (processing of determining whether incision of the target site LT has been completed) according to the type of the treatment device 40 can be performed.

Sixth Embodiment

Next, a sixth embodiment will be explained.

In the following explanation, identical reference symbols are given to components similar to those of the first embodiment described above, and their detailed explanation will be omitted or simplified.

Figure 18:
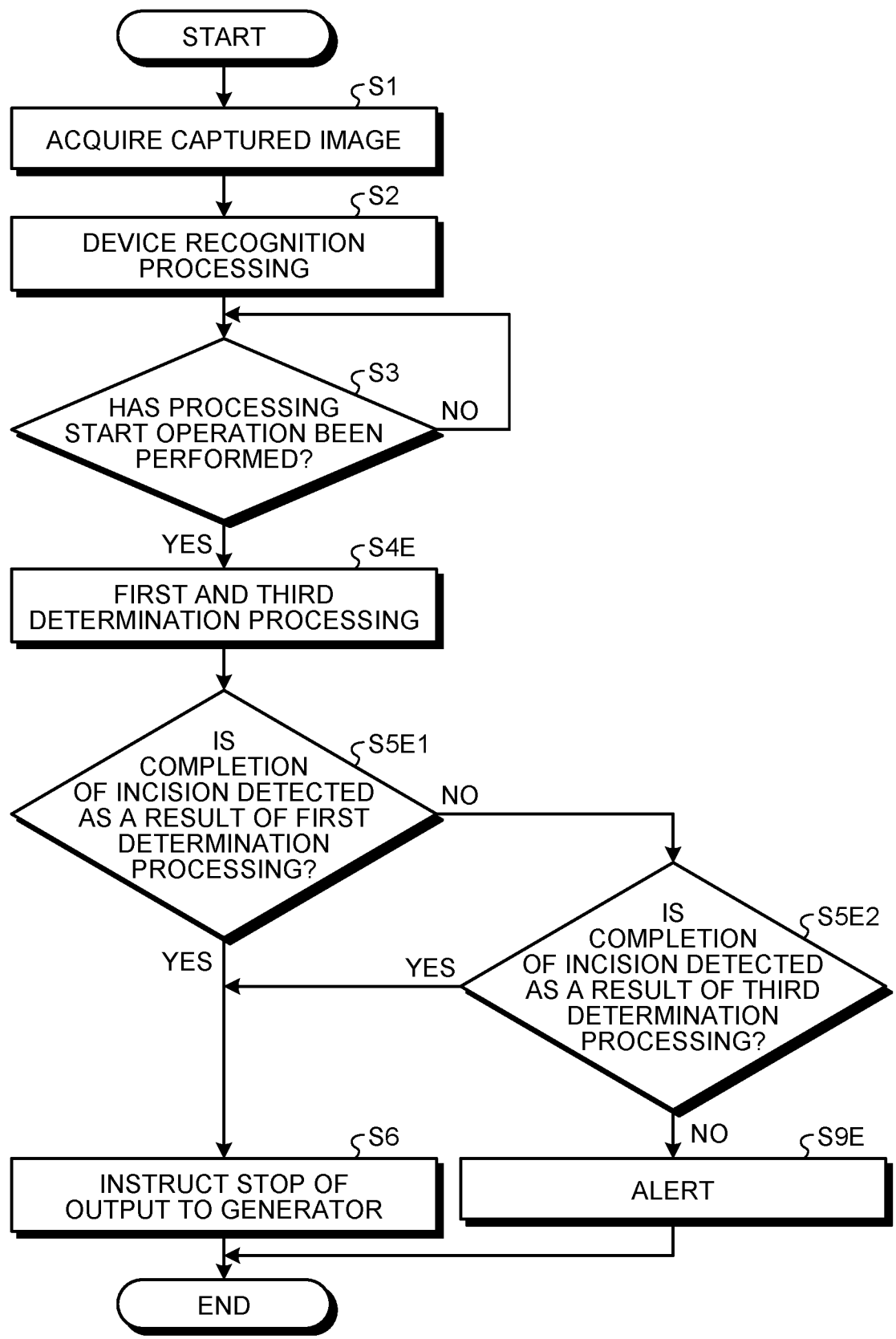
FIG. 18 is a flowchart illustrating a control method according to a sixth embodiment.

FIG. 18 is a flowchart illustrating a control method according to the sixth embodiment. In the sixth embodiment, as illustrated in FIG. 18, the control method performed by the first processor 225 is different from that of the first embodiment described above.

In the control method according to the sixth embodiment, as illustrated in FIG. 18, steps S4E, S5E1, and S5E2 are adopted instead of steps S4, S5 in the control method (FIG. 2) explained in the first embodiment described above, and step S9E is added. In the following, steps S4E, S5E1, S5E2, S9E will be explained mainly.

Step S4E is performed when it is determined that the processing start operation has been performed (step S3: YES).

Specifically, the first processor 225 performs the first determination processing (step S4) explained in the first embodiment described above, and the third determination processing (step S4B) explained in the third embodiment described above in parallel (step S4E).

When completion of incision of the target site LT is detected as a result of the first determination processing (step S5E1: YES), the first processor 225 shifts to step S6.

On the other hand, even when completion of incision of the target site LT cannot be detected as a result of the first determination processing (step S5E1: NO), if completion of incision of the target site LT is detected as a result of the third determination processing (step S5E2: YES), the first processor 225 shifts to step S6.

When completion of incision of the target site LT cannot be detected as a result of the first and the third determination processing (steps S5E1, S5E2: NO), the first processor 225 controls operation of the display device 3, and causes the display device 3 to display an alert (image) indicating that completion of incision of the target site LT cannot be detected (step S9E).

As for the alert, in addition to displaying on the display device 3, it may be configured to output the alert from a speaker, or to output the alert by lighting or flashing an LED or the like arranged on the control device 22.

According to the sixth embodiment explained above, besides effects similar to those of the first and the third embodiments described above, following effects are obtained.

When the typical phenomenon that occurs at the time of incision of the target site LT is a phenomenon that the scope 21 moves in a direction of the optical axis, completion of incision of the target site LT cannot be detected by the first determination processing even though the target site has been incised.

In the control device 22 according to the sixth embodiment, the first and the third determination processing is performed in parallel (step S4E), and even when completion of incision of the target site LT cannot be detected as a result of the first determination processing (step S5E1: NO), if completion of incision of the target site LT is detected as a result of the third determination processing (step S5E2: YES), supply of an electric power to the treatment device 40 is stopped (step S6). Therefore, even when the typical phenomenon that occurs at the time of incision of the target site LT in the treatment device 40 is a phenomenon that the scope 21 moves in the direction of optical axis, completion of incision of the target site LT can be detected, and the supply of an electric power to the treatment device 40 can be stopped.

Other Embodiments

The embodiments to implement the disclosure have so far been explained, but the disclosure is not to be limited to the first to the sixth embodiments.

In the first to the sixth embodiments, as the determination value, the moving speed of the treatment device 40, the first and the second moving speed of the treatment device 40, the fluctuation speed of pixel level, and the moving speed of the target site LT have been adopted, but it is not limited thereto. For example, a moving amount of the feature point P1

(corresponding to a moving amount of the treatment device 40), the distance D2 between the feature points P2 and P3 (corresponding to a moving amount of the treatment device 40), the distance D3 between the feature points P2 and P4 (corresponding to a moving amount of the treatment device 40), a mean value of pixel level of respective pixels in the area Ar2, and the distance D4 between the feature points P5 and P6 (corresponding to a moving amount of the target site LT) after the treatment energy is started to be applied to the target site LT may be adopted as the determination value. Moreover, as the determination value, the moving speed of the treatment device 40, the first and the second moving speeds of the treatment device 40, the fluctuation speed of pixel level, and the moving speed of the target site LT, and the moving amount of the feature point P1, the distance D between the feature points P2 and P3, the distance D3 between the feature points P2, and P4, the mean value of pixel level of the respective pixels in the area Ar2, and the distance D4 between the feature points P5 and P6 after the start of application of a treatment energy to the target site LT may be combined.

Figure 19:
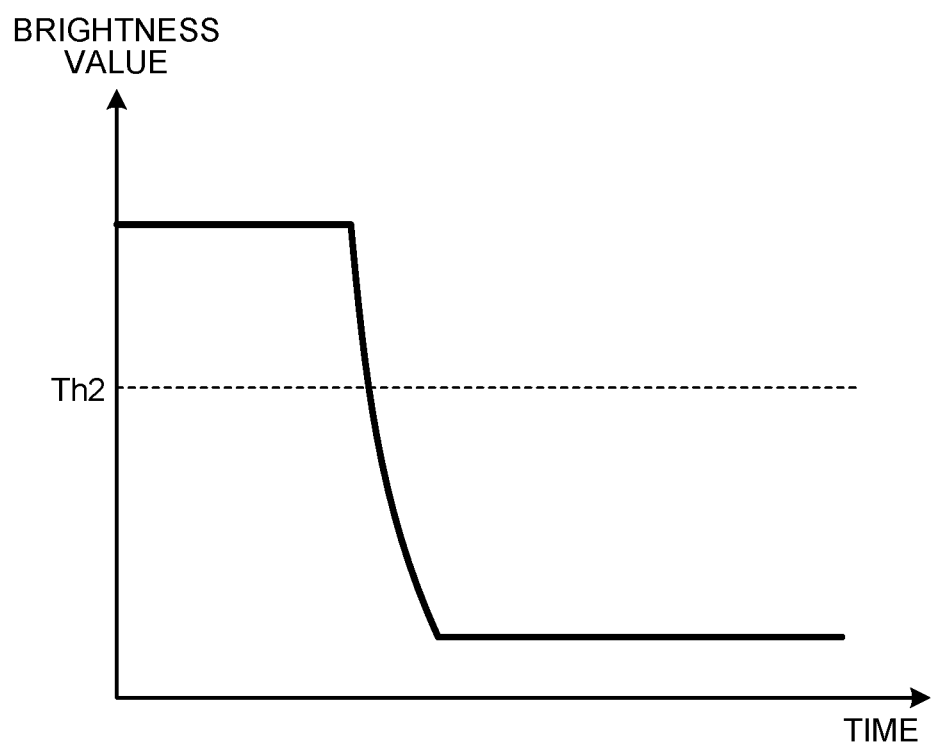
FIG. 19 is a diagram illustrating a modification of the third embodiment.

FIG. 19 is a diagram illustrating a modification of the third embodiment. Specifically, FIG. 19 is a diagram illustrating a behavior of the mean value of pixel level (brightness value) of respective pixels in the area Ar2 after the start of application of the treatment energy to the target site LT.

For example, if the mean value of pixel level (brightness value) of the respective pixels in the area Ar2 is adopted as the determination value, when the target site LT is incised, the target site LT moves from the area Ar2 and disappears therefrom, and a portion less likely to be illuminated by the illumination light then enters the area Ar2. Therefore, when the target site LT is incised, the mean value decreases to be equal to or lower than the second threshold Th2 as illustrated in FIG. 19. That is, the first processor 225 detects completion of incision of the target site LT when the mean value becomes equal to or lower than the second threshold Th2.

In the second embodiment described above, as the determination value, the first and the second moving speeds based on the distances D2, D3 from the feature points P3, P4 in the target site LT to the feature point P2 in the treatment device 40 are adopted, but it is not limited thereto. Three or more moving speeds based on three or more distances from three or more feature points in the target site LT to one feature point in the treatment device 40 may be adopted as the determination value. Moreover, conversely, plural moving speeds based on plural distances from one feature point in the target site LT to plural feature points in the treatment device 40 may be adopted as the determination value. Furthermore, plural moving speeds based on plural distances from plural feature points in the target site LT to plural feature points in the treatment device 40 may be adopted as the determination value.

In the fifth embodiment described above, a configuration in which instead of the first determination processing (steps S4, S5), the second determination processing (steps S4A, S5A) is performed may be adopted. Moreover, in the fifth embodiment described above, a configuration in which instead of the third determination processing (steps S4B, S5B), the fourth determination processing (steps S4C, S5C) is performed may be adopted.

Similarly, in the sixth embodiment, a configuration in which the second determination processing is performed instead of the first determination processing may be adopted. Furthermore, in the sixth embodiment, a configuration in which the fourth determination processing is performed instead of the third determination processing may be adopted.

In the first to the sixth embodiments, the common generator 43 is used for the first and the second treatment devices 41, 42, but it is not limited thereto, and generators may be provided respectively to the first treatment device 41 and the second treatment device 42.

In the first to the sixth embodiments described above, the scope 21 is constituted of a flexible endoscope, but it is not limited thereto. Instead of the scope 21, a component combining a rigid endoscope and a camera head may be adopted.

In the first to the sixth embodiments described above, as the treatment instrument, a robotics treatment instrument (for example, refer to Japanese Patent No. 4960112) that includes plural arms, a joint portion that connects the arms in a relatively movable manner, and a driving mechanism that drives the arms by actuating the joint portion may be adopted.

In the first to the sixth embodiments described above, the device recognition processing (step S2) may be performed, similarly to the type determination processing (step S7D), by image recognition using a training model (image recognition using AI).

In the first to the sixth embodiments described above, the control method illustrated in FIG. 2, FIG. 7, FIG. 10, FIG. 14, FIG. 17, and FIG. 18 may be performed by the second processor 432. That is, it may be configured to make the second processor 432, not the first processor 225, function as the processor.

In the first to the sixth embodiments described above, the control method illustrated in FIG. 2, FIG. 7, FIG. 10, FIG. 14, FIG. 17, and FIG. 18 may be performed by plural processors. That is, the processor according to the disclosure may be constituted of plural processors, not limited to one.

According to the treatment system, the control device, and the control method according to the disclosure, it is possible to avoid supply of unnecessary power to a treatment instrument, and to reduce a load on the treatment instrument.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment system comprising:
    a treatment instrument having an end effector configured to apply a treatment energy to a living tissue;
    an imaging device configured to generate an image of the living tissue; and
    a processor configured to control the imaging device that is also configured to:
        acquire the image,
        set, based on the image, a reference point on the living tissue adjacent to the end effector,
        calculate, based on the image, at least one of a moving amount or a moving speed of a specific point on the end effector after the treatment energy is started to be applied to the living tissue, relative to the reference point,
        determine that incision of the living tissue has been completed based on the at least one of the moving amount or the moving speed, the moving amount or the moving speed indicating that the end effector moved away from the reference point, and in response to determining that the incision of the living tissue has been completed, execute an instruction to stop supply of an electric power to the treatment instrument.

2. The treatment system according to claim 1, further comprising a memory configured to store a first threshold, wherein:
the end effector includes a gripper configured to grip the living tissue, the end effector configured to apply the treatment energy to the living tissue through the gripper,
the specific point comprises the gripper, and
the processor is configured to:
determine that the incision of the living tissue has been completed when the at least one of the moving amount or the moving speed becomes equal to or higher than the first threshold.

3. The treatment system according to claim 2, wherein the processor is configured to detect an object that extends linearly from an edge of the image out of a plurality of objects shown in the image.

4. The treatment system according to claim 2, wherein the processor is configured to detect the gripper from a plurality of objects shown in the image, based on a color in the image.

5. The treatment system according to claim 1, further comprising a memory configured to store a second threshold, wherein:
the processor is configured to:
calculate, based on the image, at least one of a pixel level of an area adjacent to the end effector or a fluctuation speed of the pixel level, and
determine whether the incision of the living tissue has been completed by comparing the at least one of the pixel level or the fluctuation speed to the second threshold.

6. The treatment system according to claim 1, further comprising a memory configured to store a third threshold, wherein:
the processor is configured to:
calculate, based on the image, at least one of a moving amount or a moving speed of the living tissue adjacent to the end effector after the treatment energy is started to be applied to the living tissue, and
determine that the incision of the living tissue has been completed when the at least one of the moving amount or the moving speed of the living tissue adjacent to the end effector becomes equal to or larger than the third threshold value.

7. The treatment system according to claim 6, wherein the processor is configured to calculate at least one of a moving amount or a moving speed among a plurality of feature points of the living tissue adjacent to the end effector to determine whether the incision of the living tissue has been completed.

8. The treatment system according to claim 1, wherein the processor is configured to:
determine a type of the treatment instrument based on the image, and
perform determination processing according to the determined type of the treatment instrument from a plurality of kinds of determination processing to determine whether the incision of the living tissue has been completed.

9. The treatment system according to claim 1, wherein the treatment energy is at least one of an ultrasonic vibration, a high-frequency electric current, or heat.

10. The treatment system according to claim 1, wherein the end effector is configured to apply the treatment energy to the living tissue while gripping the living tissue to be under tension such that a moving amount of the living tissue immediately changes when the incision of the living tissue has been completed.

11. The treatment system according to claim 1, wherein the processor is configured to recognize a type of the treatment instrument by performing image recognition that has been trained to learn a shape of the treatment instrument on objects shown in the image.

12. The treatment system according to claim 1, wherein the moving speed is calculated based on the moving amount of the specific point on the end effector.

13. The treatment system according to claim 1, wherein the moving amount is calculated based on the moving speed of the specific point on the end effector.

14. A control device comprising:
a processor configured to:
acquire an image,
set, based on the image, a reference point on a living tissue in the image adjacent to an end effector,
calculate, based on the image, at least one of a moving amount or a moving speed of a specific point on the end effector after a treatment energy is started to be applied to a living tissue, relative to the reference point,
determine that incision of the living tissue has been completed, based on the at least one of the moving amount or the moving speed, the moving amount or the moving speed indicating that the end effector moved away from the reference point; and
execute an instruction to stop supply of an electric power to a treatment instrument in response to determining that the incision of the living tissue has been completed.

15. The control device according to claim 14, wherein the processor is configured to detect an object that extends linearly from an edge of the image out of a plurality of objects shown in the image.

16. A control method, comprising:
acquiring an image;
setting, based on the image, a reference point on a living tissue in the image adjacent to an end effector;
calculating, based on the image, at least one of a moving amount or a moving speed of a specific point on the end effector after a treatment energy is started to be applied to a living tissue, relative to the reference point;
determining whether incision of the living tissue has been completed, based on the at least one of the moving amount or the moving speed, the moving amount or the moving speed indicating that the end effector moved away from the reference point; and
executing an instruction to stop supply of an electric power to a treatment instrument in response to determining that the incision of the living tissue has been completed.

17. The control method according to claim 16, further comprising detecting an object that extends linearly from an edge of the image out of a plurality of objects shown in the image.

* * * * *